(12) United States Patent
Steinmetz et al.

(10) Patent No.: US 12,070,478 B2
(45) Date of Patent: *Aug. 27, 2024

(54) CANCER IMMUNOTHERAPY USING VIRUS PARTICLES

(71) Applicant: CASE WESTERN RESERVE UNIVERSITY, Cleveland, OH (US)

(72) Inventors: Nicole F. Steinmetz, San Diego, CA (US); Karin L. Lee, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/115,066

(22) Filed: Feb. 28, 2023

(65) Prior Publication Data

US 2024/0058401 A1 Feb. 22, 2024

Related U.S. Application Data

(63) Continuation of application No. 16/492,884, filed as application No. PCT/US2018/022023 on Mar. 12, 2018, now Pat. No. 11,590,183, which is a continuation-in-part of application No. 15/589,677, filed on May 8, 2017, now Pat. No. 10,639,363.

(60) Provisional application No. 62/469,869, filed on Mar. 10, 2017.

(51) Int. Cl.
*A61K 35/76* (2015.01)
*A61K 31/704* (2006.01)
*A61K 39/12* (2006.01)
*A61K 39/39* (2006.01)
*A61P 35/00* (2006.01)
*C12N 7/00* (2006.01)
*A61K 45/06* (2006.01)

(52) U.S. Cl.
CPC ............ *A61K 35/76* (2013.01); *A61K 31/704* (2013.01); *A61K 39/12* (2013.01); *A61K 39/39* (2013.01); *A61P 35/00* (2018.01); *A61K 45/06* (2013.01); *C12N 2770/26011* (2013.01); *C12N 2770/26023* (2013.01); *C12N 2770/26033* (2013.01); *C12N 2770/26042* (2013.01); *C12N 2770/40023* (2013.01)

(58) Field of Classification Search
None
See application file for complete search history.

(56) References Cited

FOREIGN PATENT DOCUMENTS

WO WO 2013/181557 A1 * 12/2013

OTHER PUBLICATIONS

Lebel et al. (Nano Lett. 2016, 16, 1826-1832).*
Aljabali et al. (Mol. Pharmaceutics 2013, 10: 3-10).*

* cited by examiner

*Primary Examiner* — Nianxiang Zou
(74) *Attorney, Agent, or Firm* — Tarolli, Sundheim, Covell & Tummino LLP

(57) ABSTRACT

A method of treating cancer in a subject in need thereof includes administering in situ to the cancer a therapeutically effective amount of a virus or virus-like particle.

20 Claims, 27 Drawing Sheets

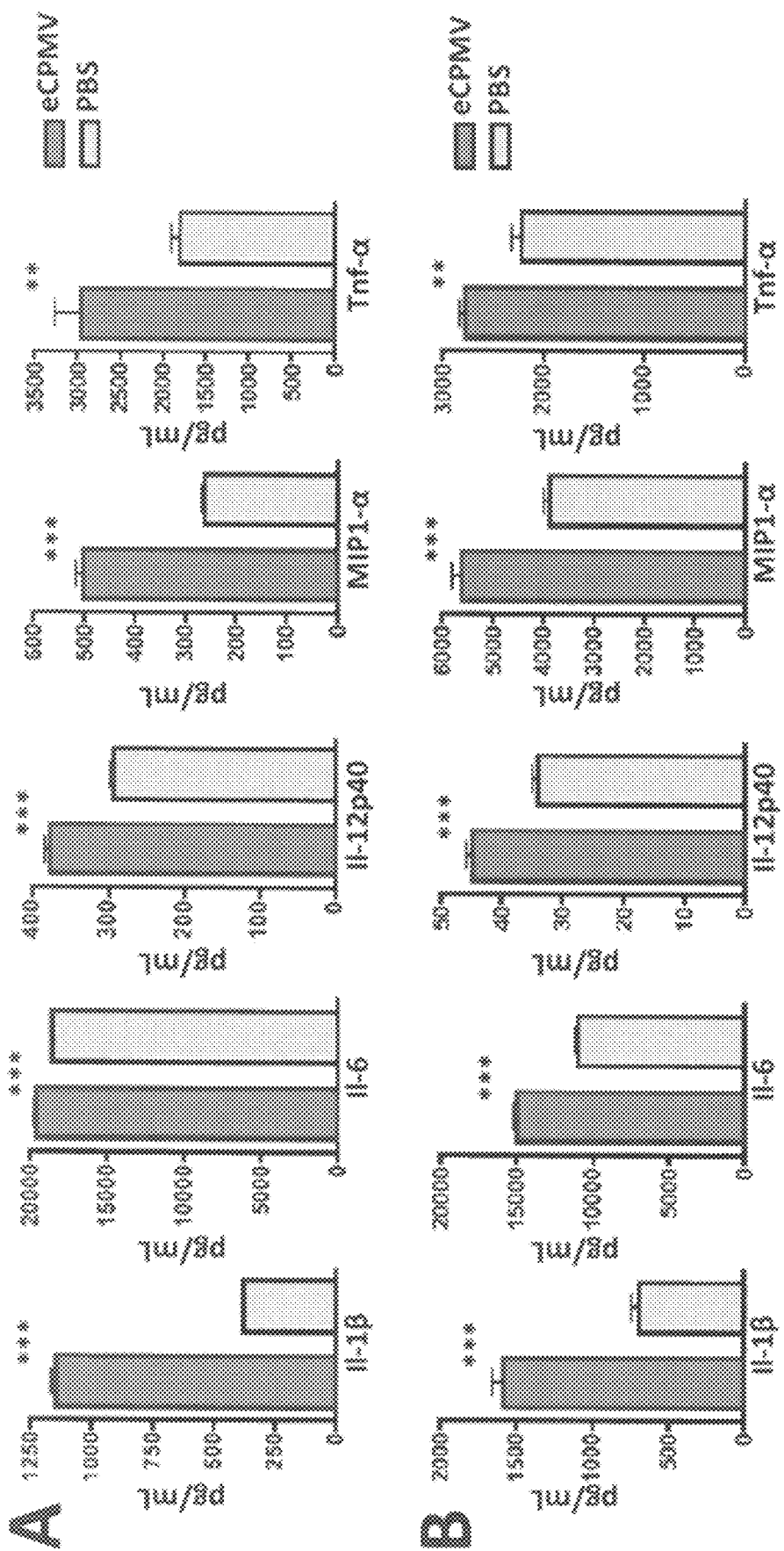
Figs. 1A-B

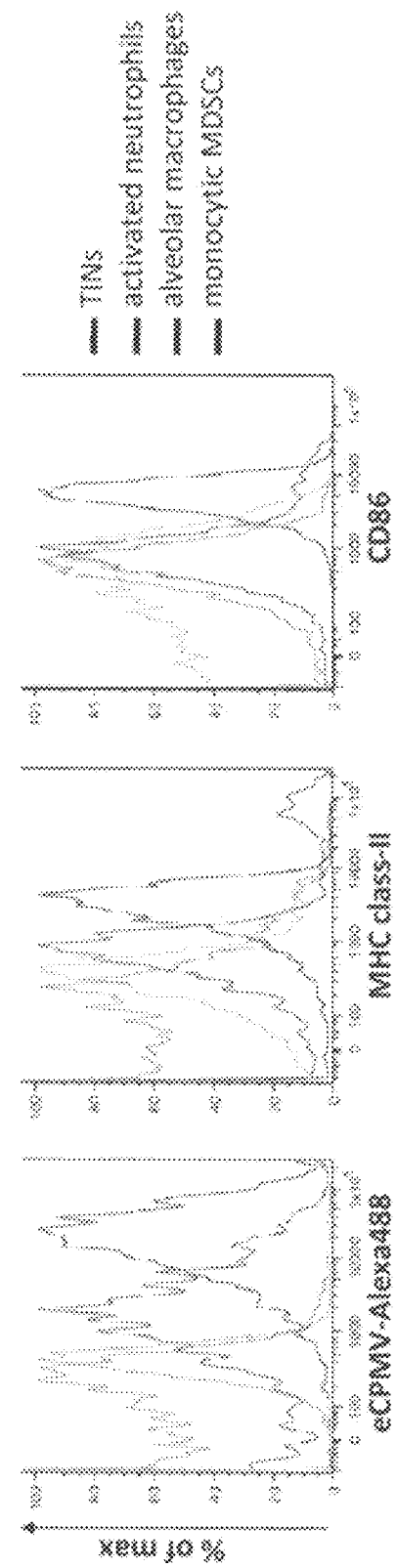
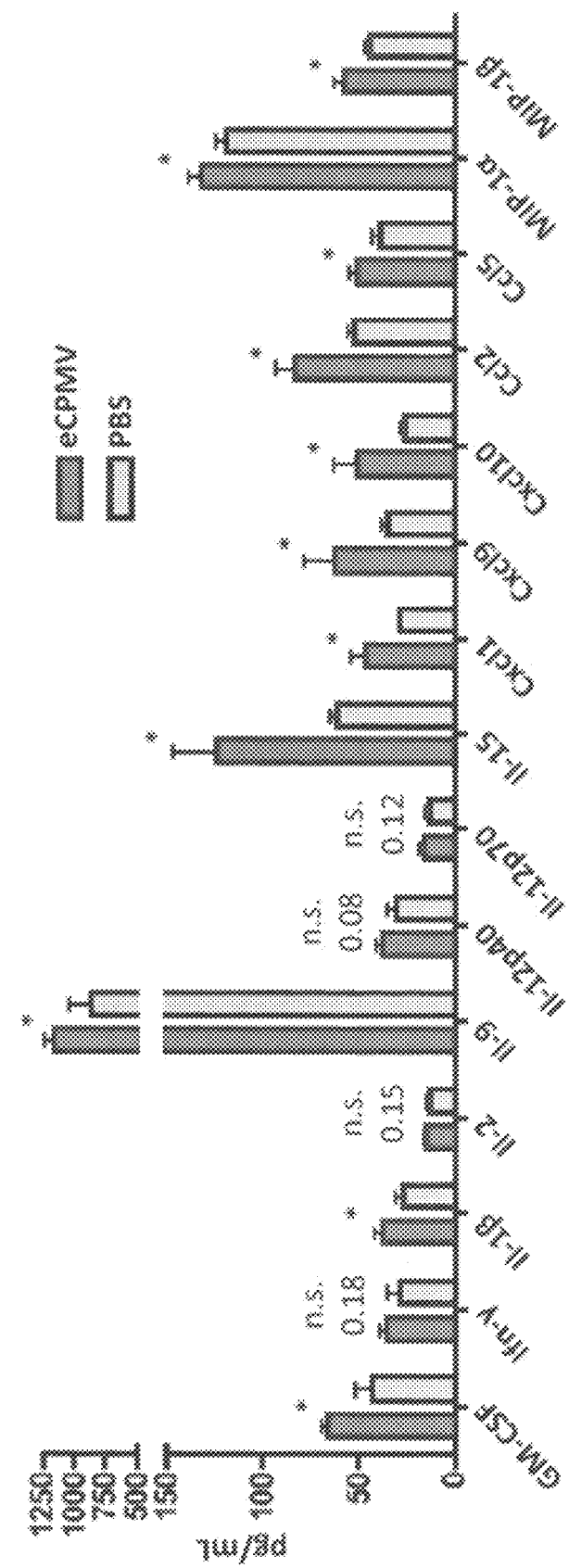
Figs. 2C-D

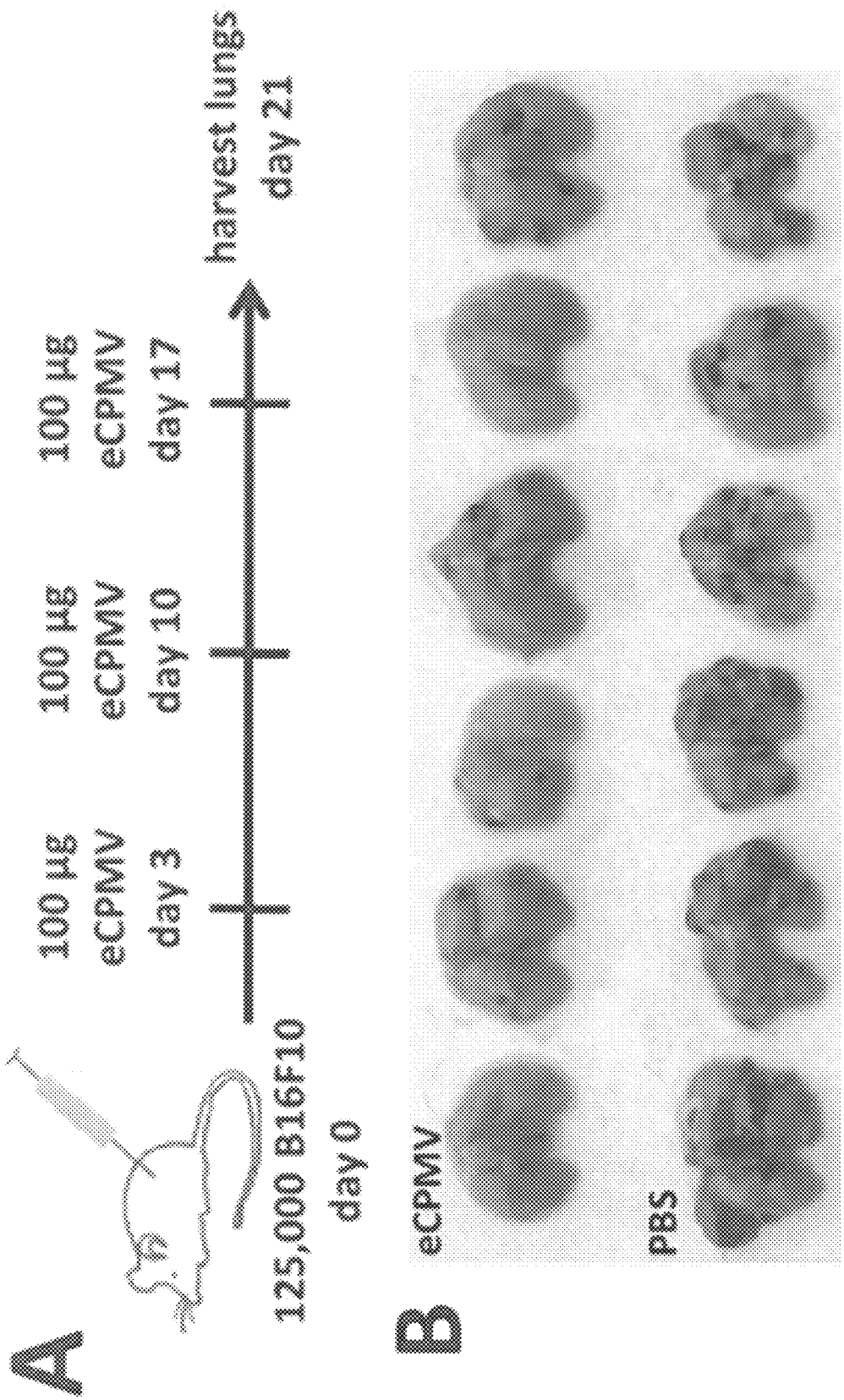
Figs. 3A-B

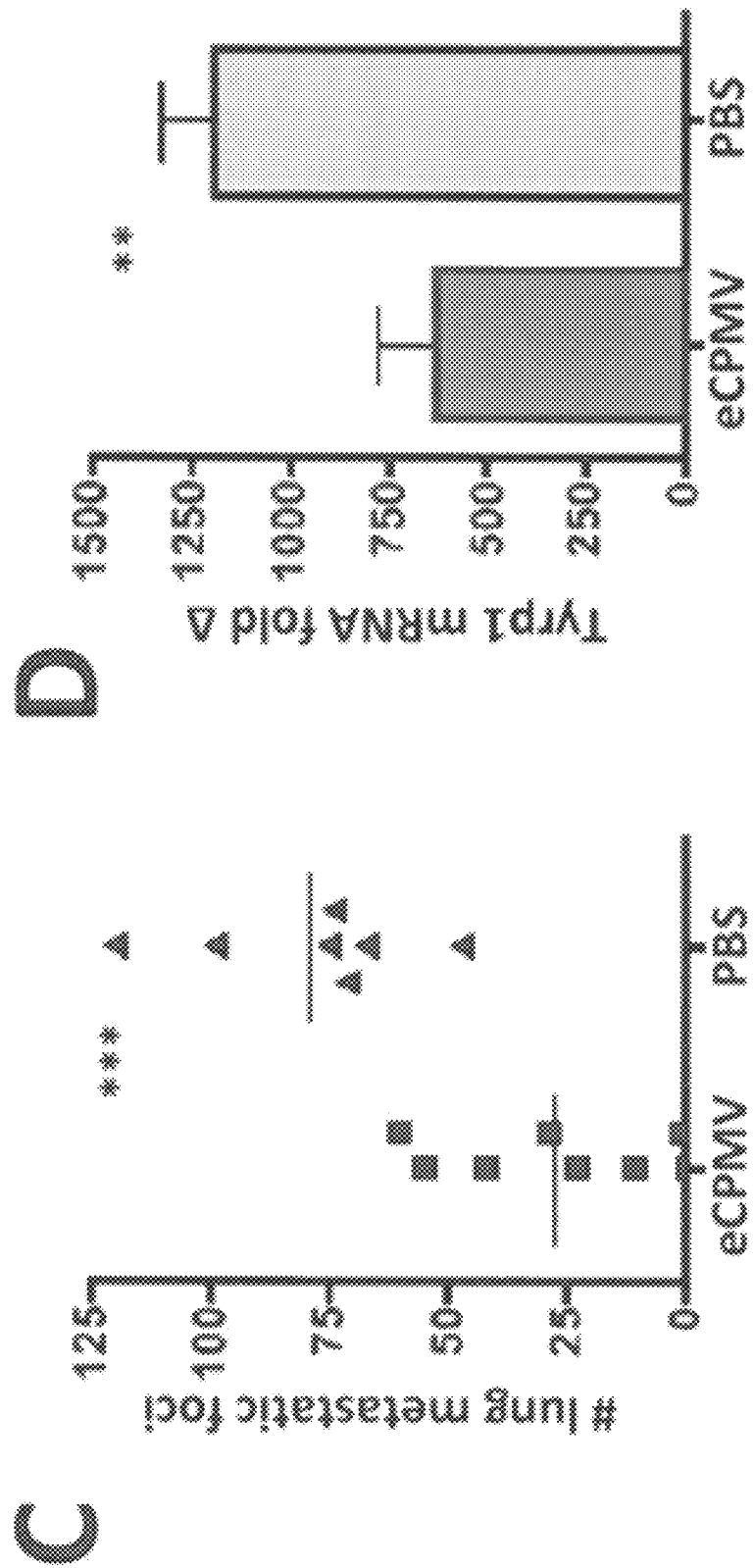
Figs. 3C-D

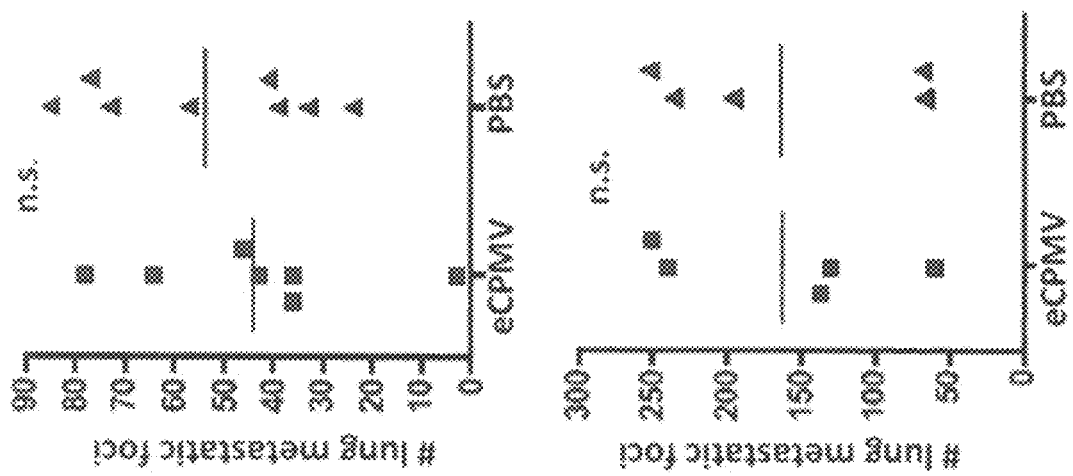
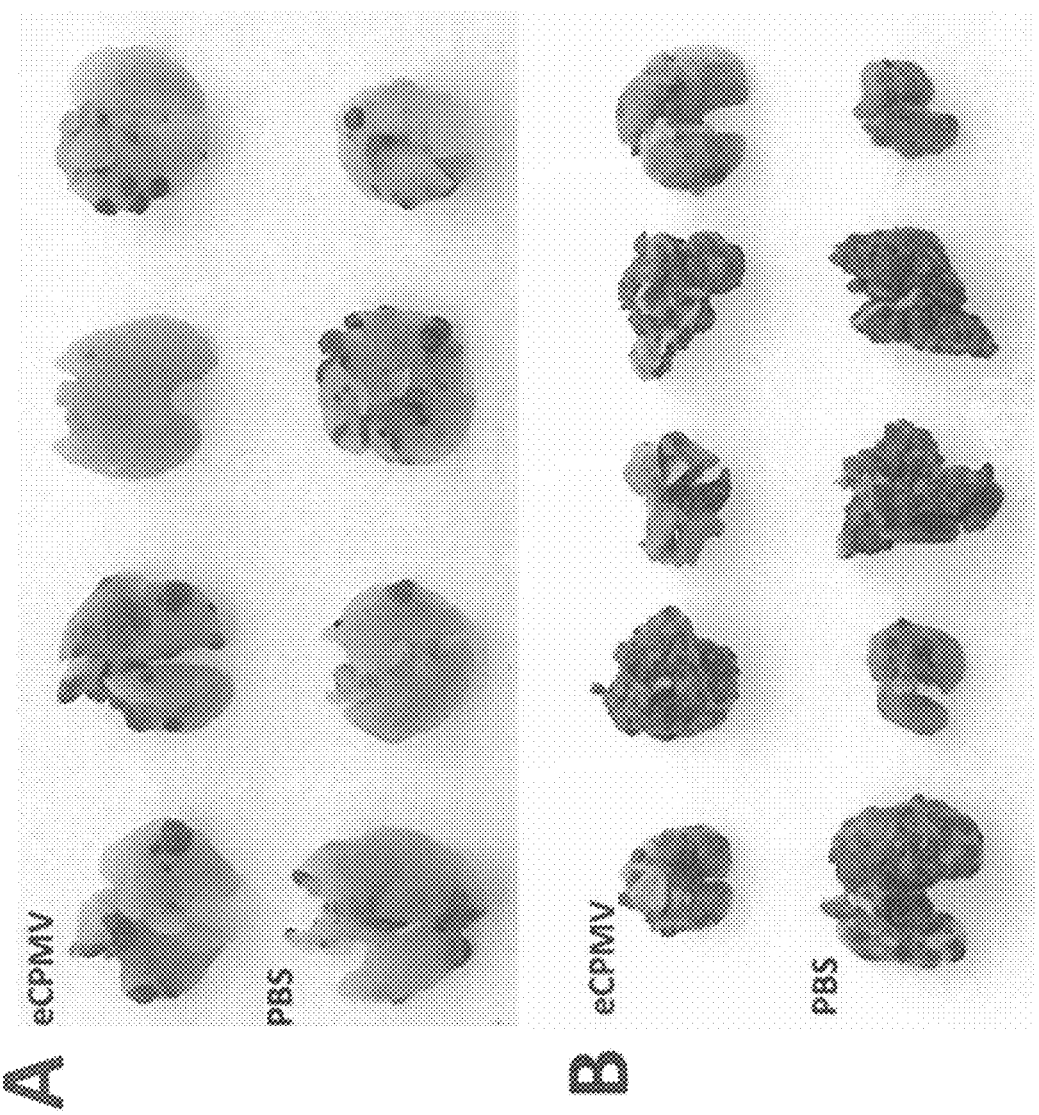
Figs. 4A-B

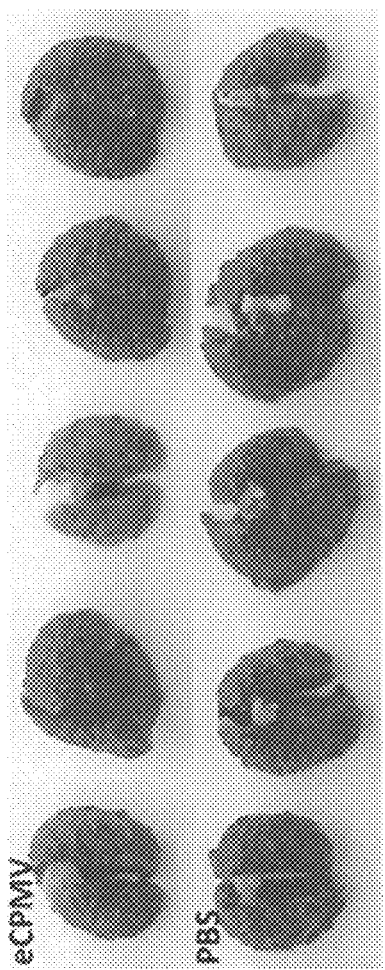
Fig. 4C
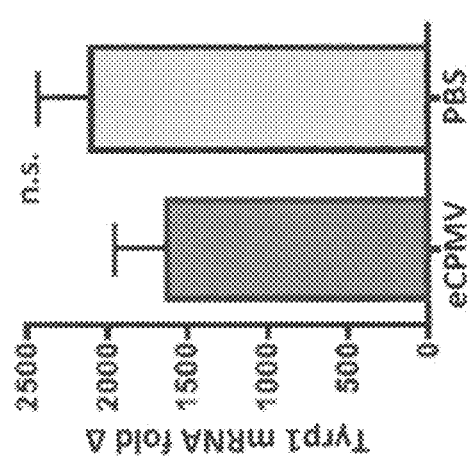
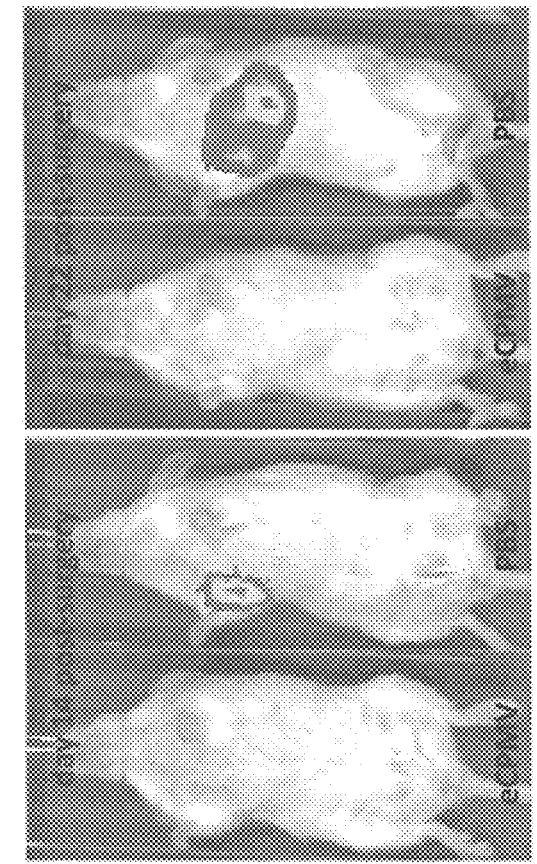
Fig. 5A
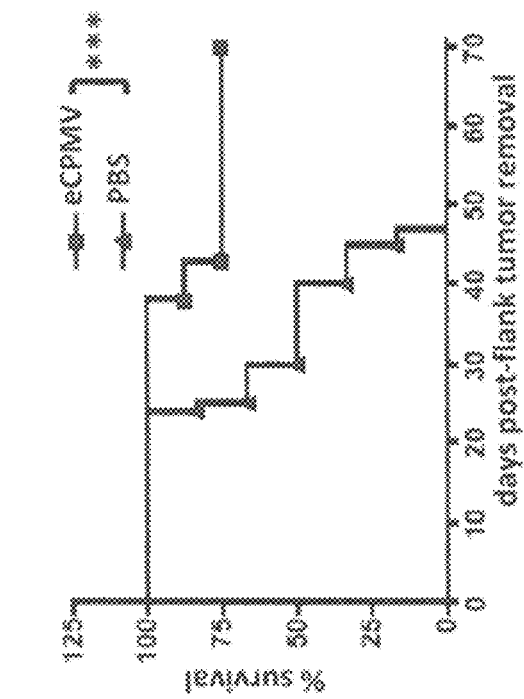

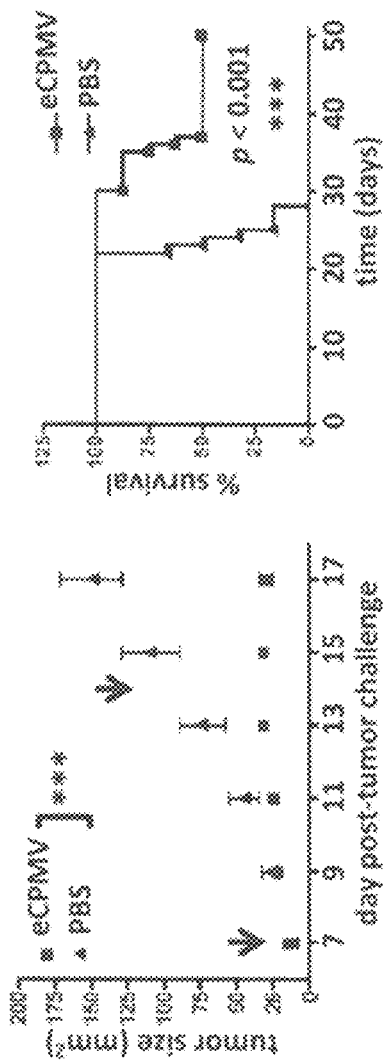
Fig. 5B
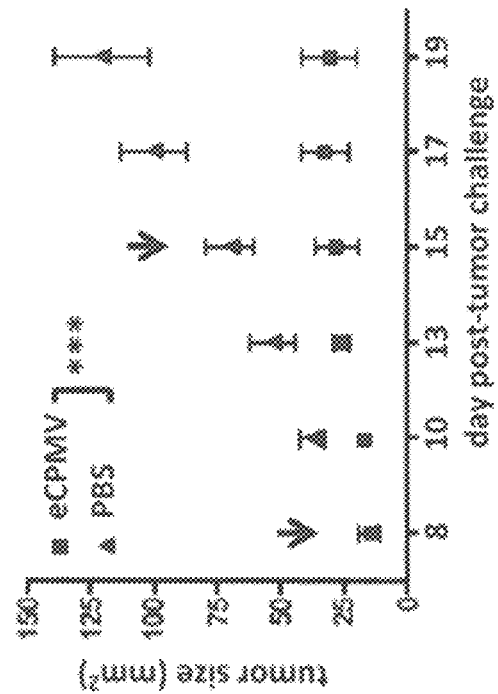
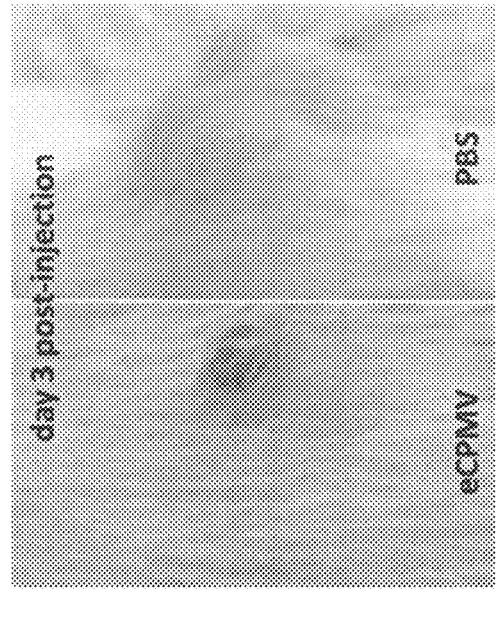
Fig. 5C

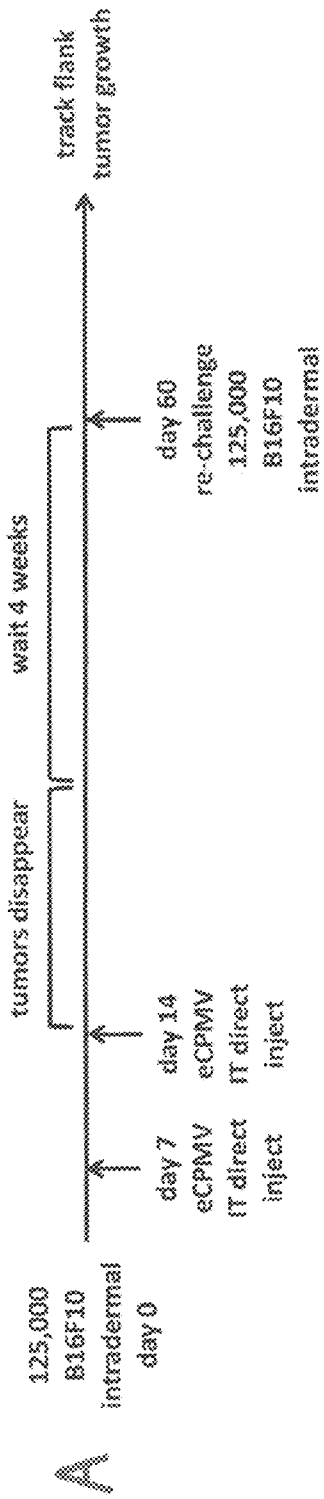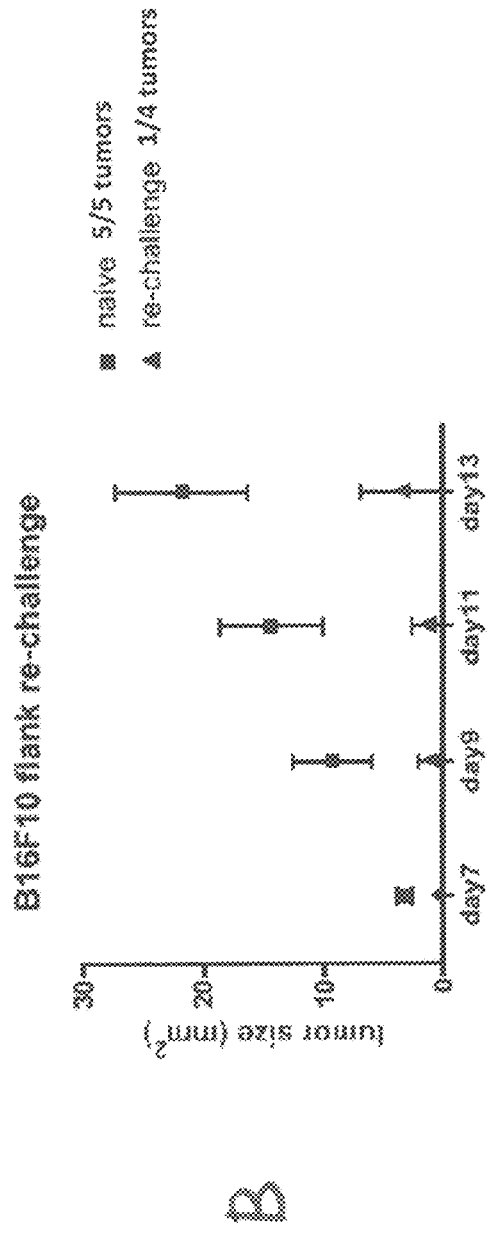
Figs. 6A-B

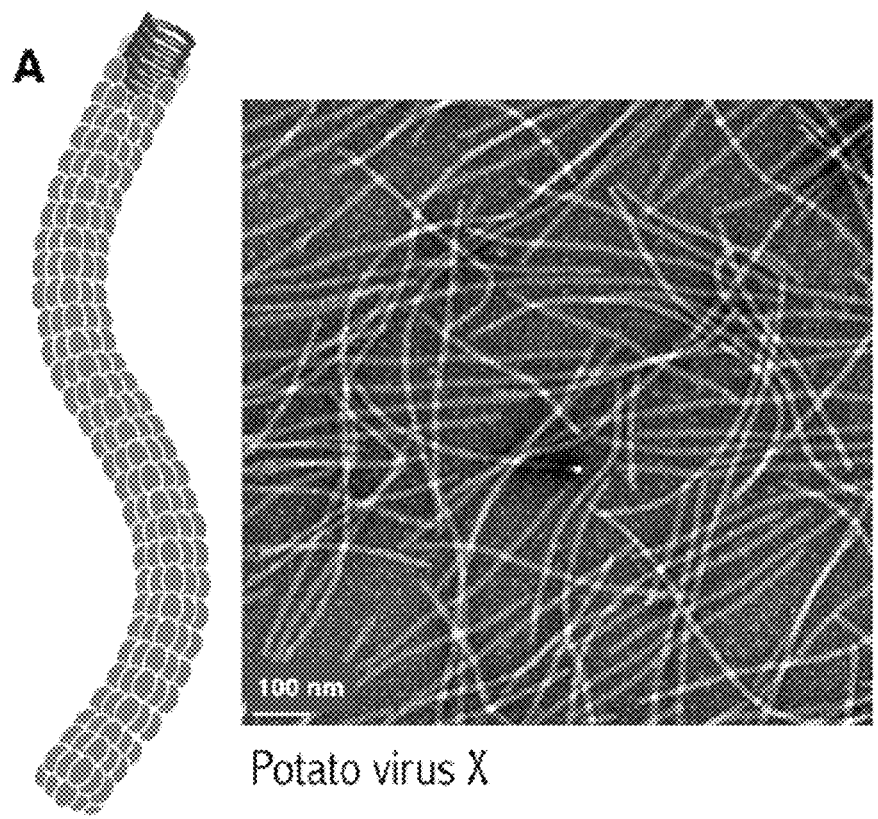
Potato virus X
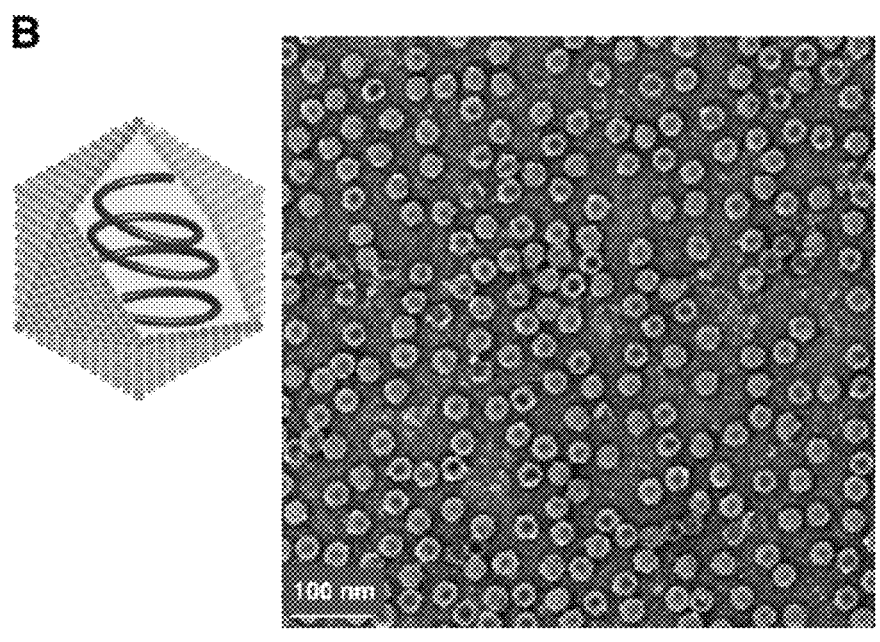
Cowpea mosaic virus
Figs. 7A-B

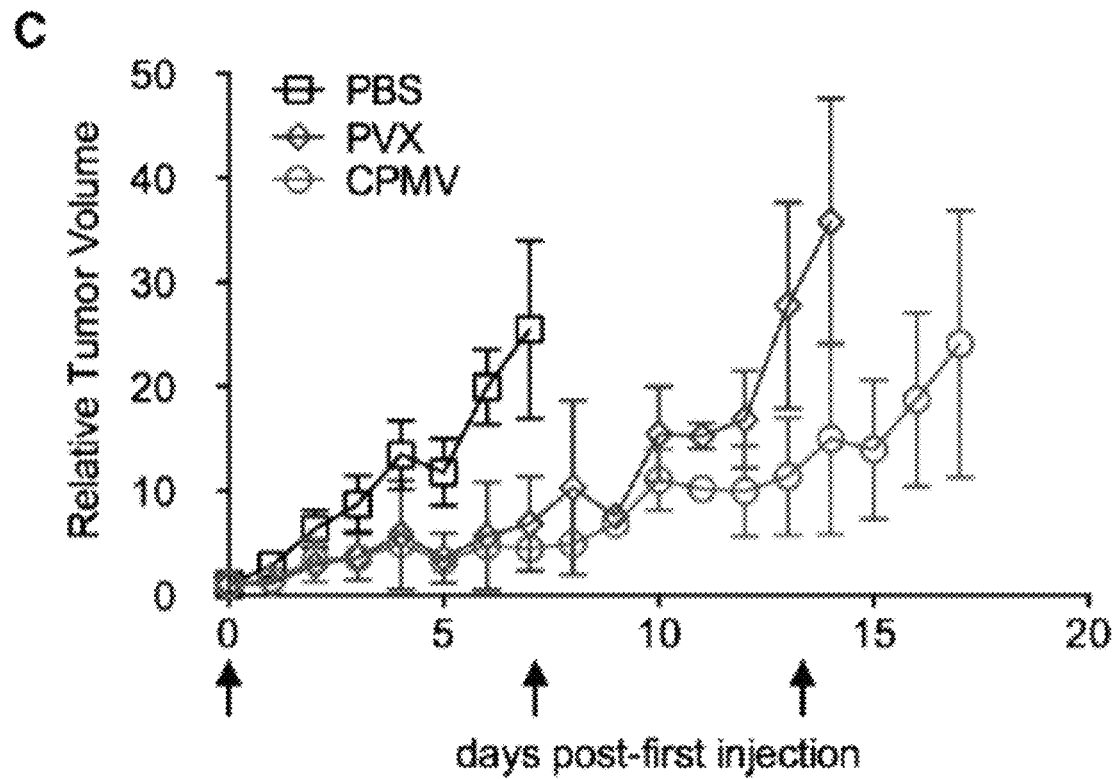
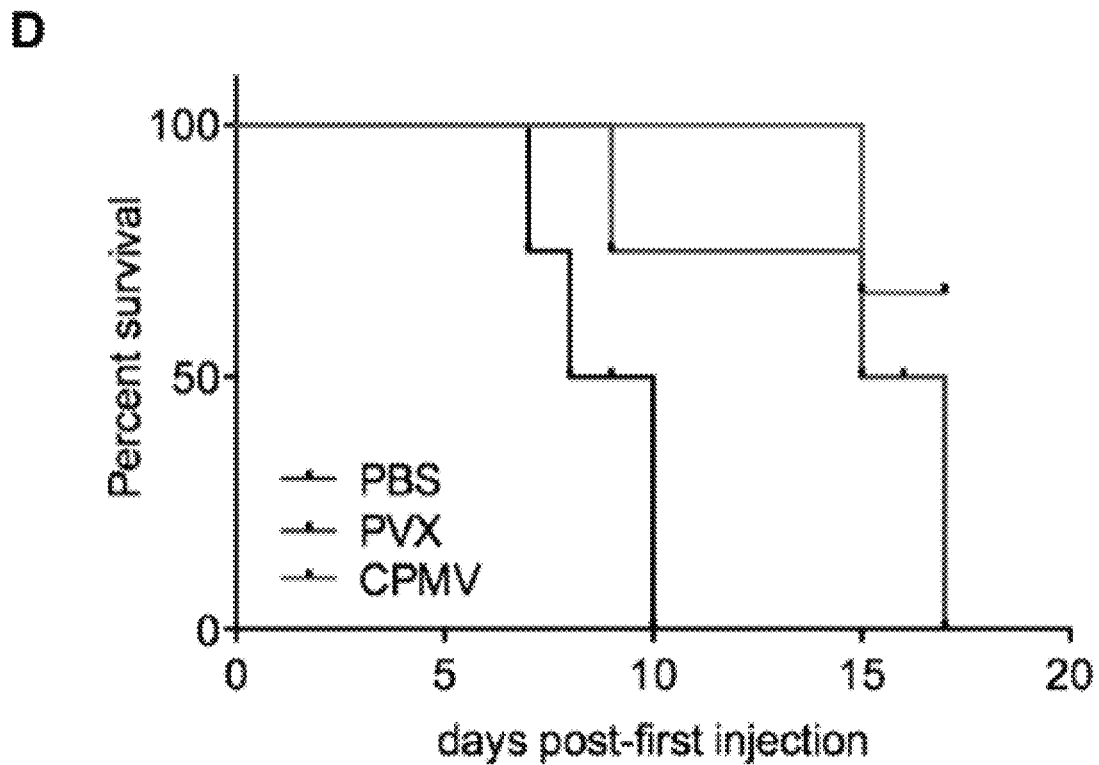
Figs. 7A-D

Figs. 8A-B

C
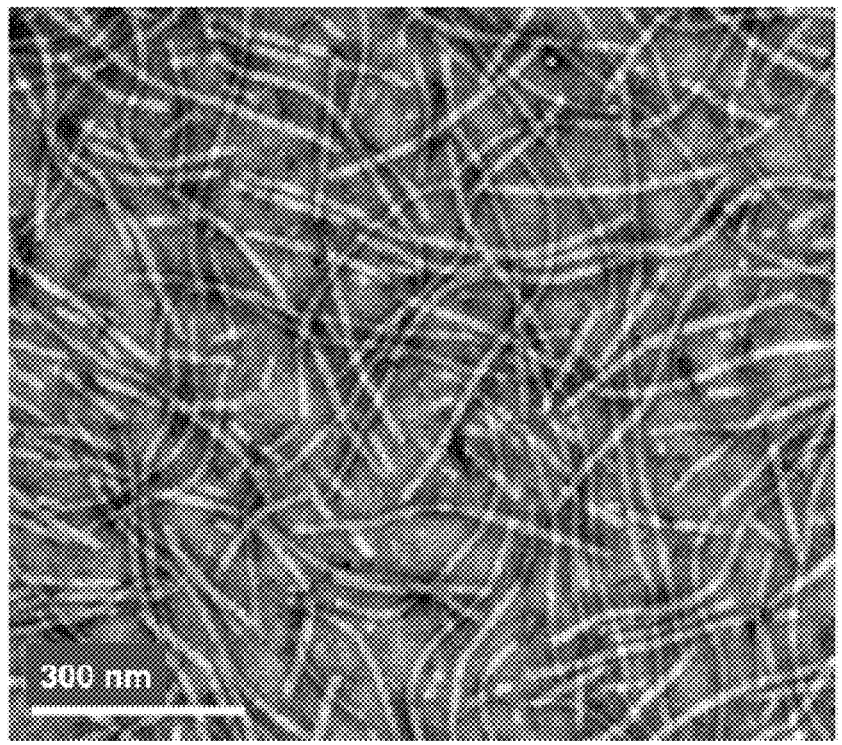
D
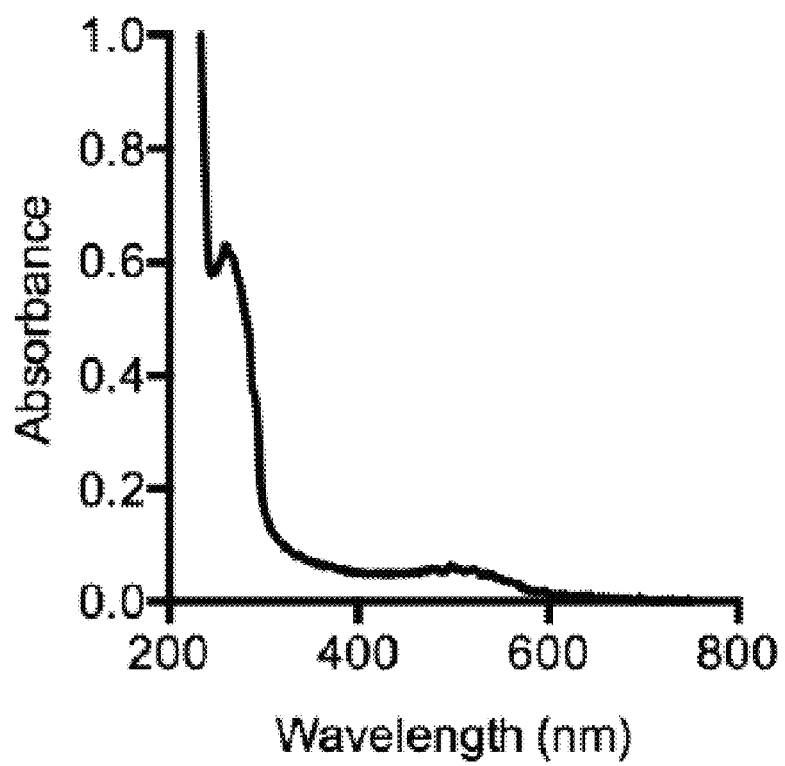
Figs. 8C-D

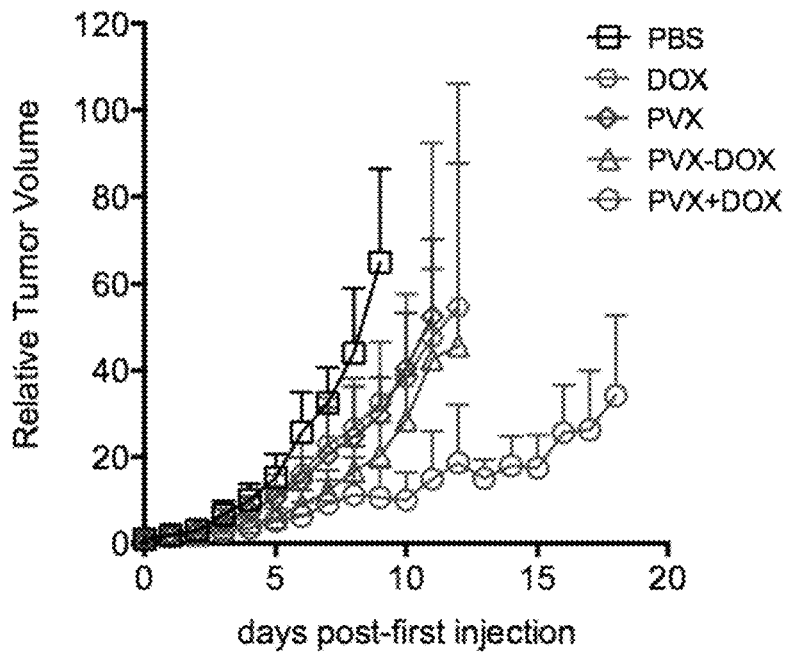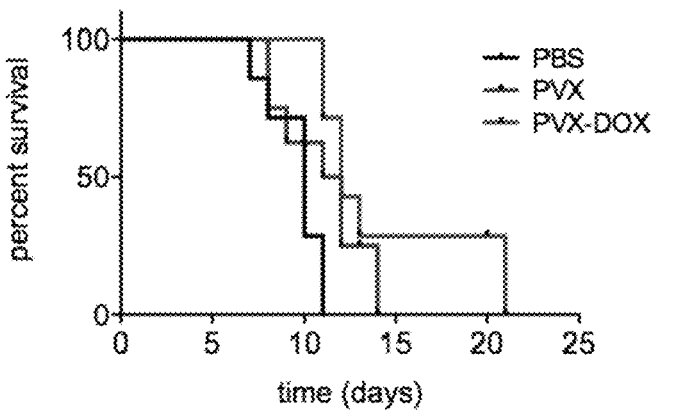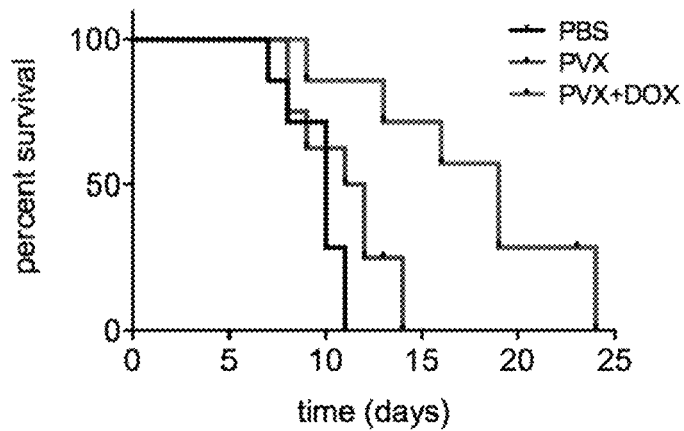
Figs. 9A-B

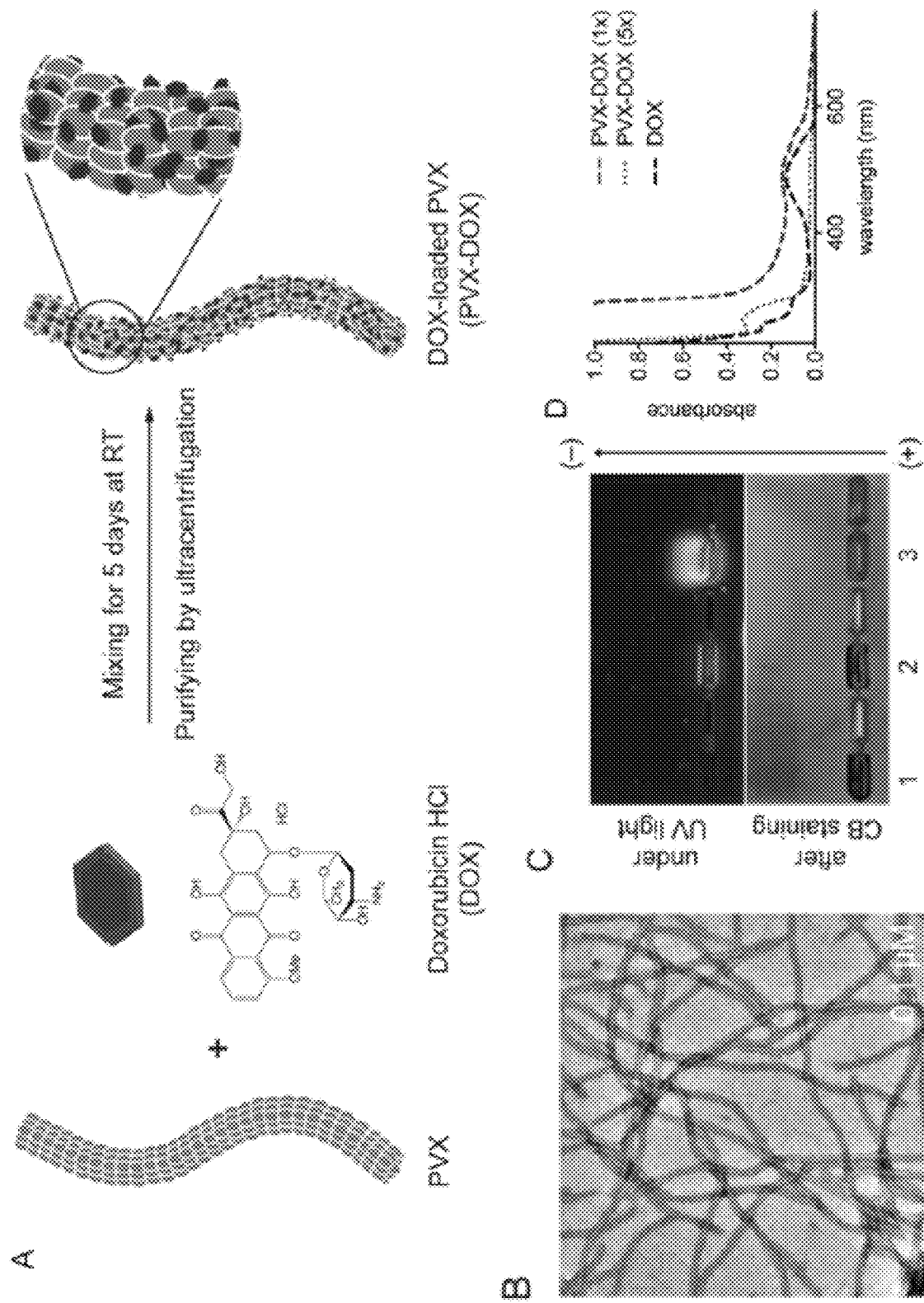
Figs. 11A-D

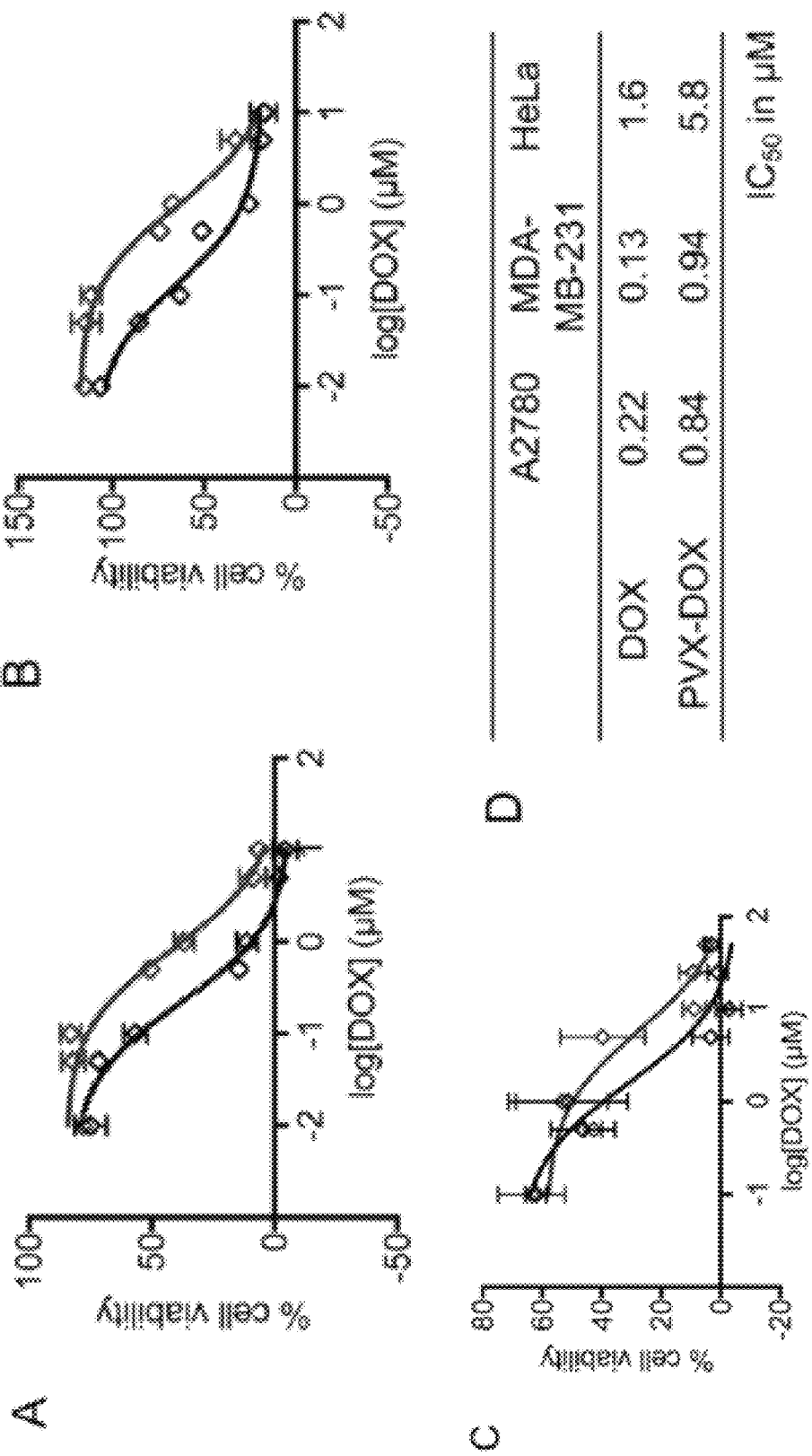
Figs. 12A-D

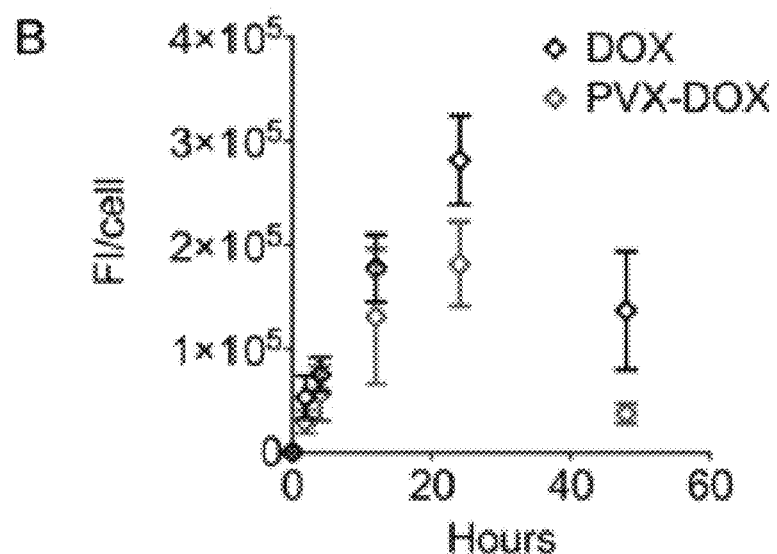
Fig. 13B
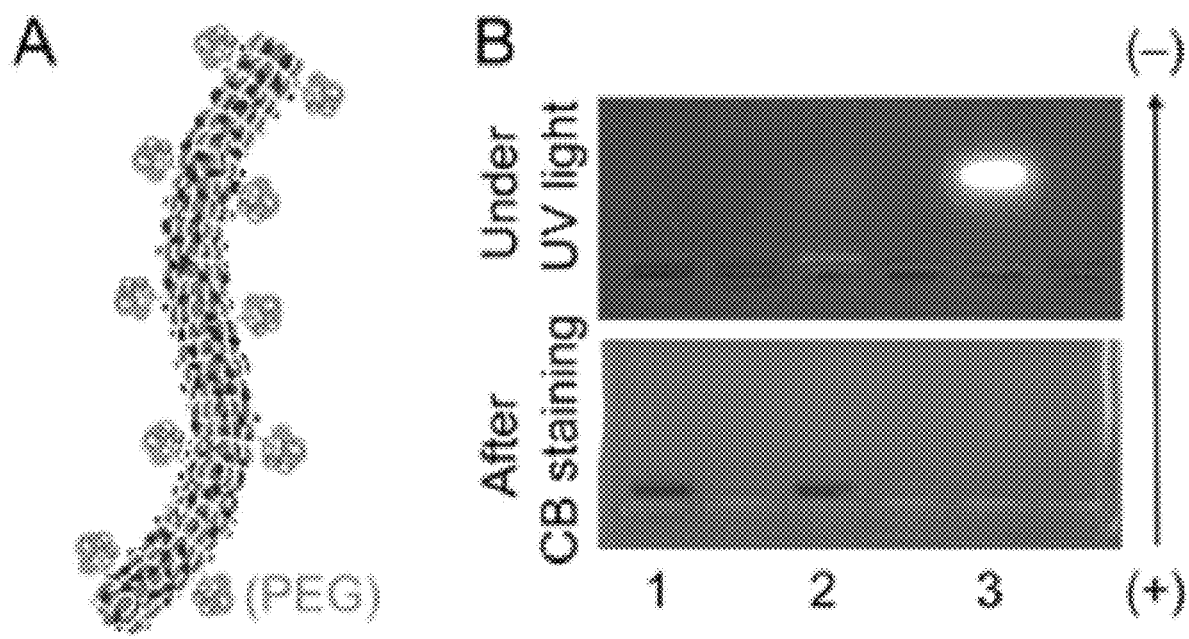
Figs. 14A-B

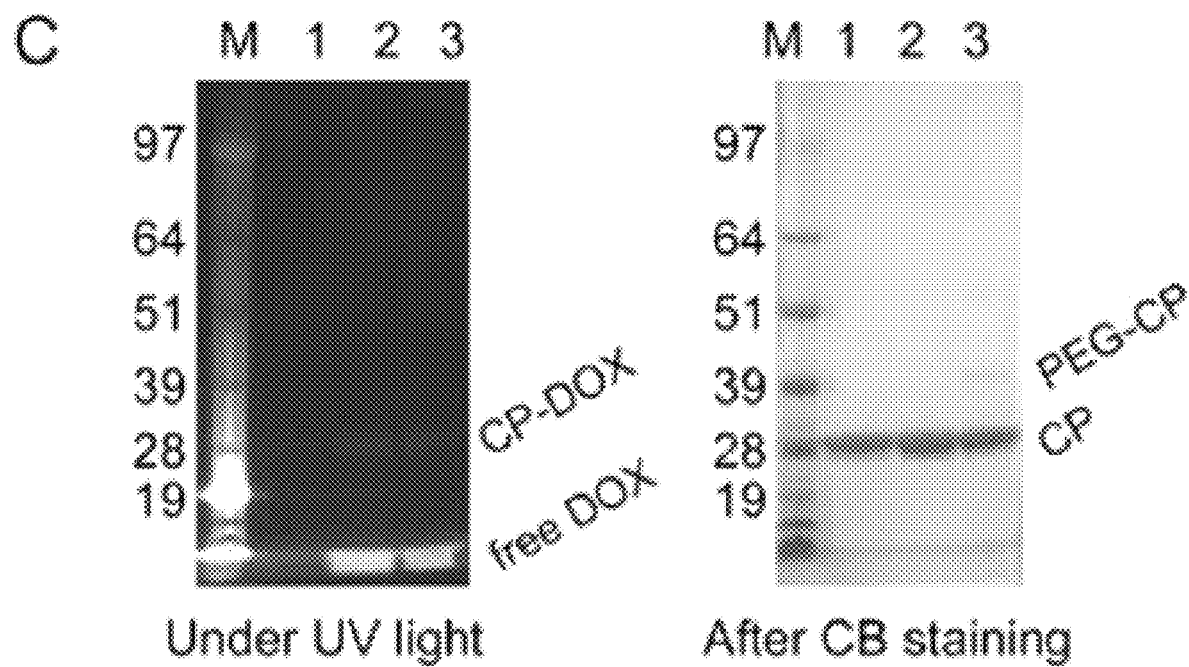
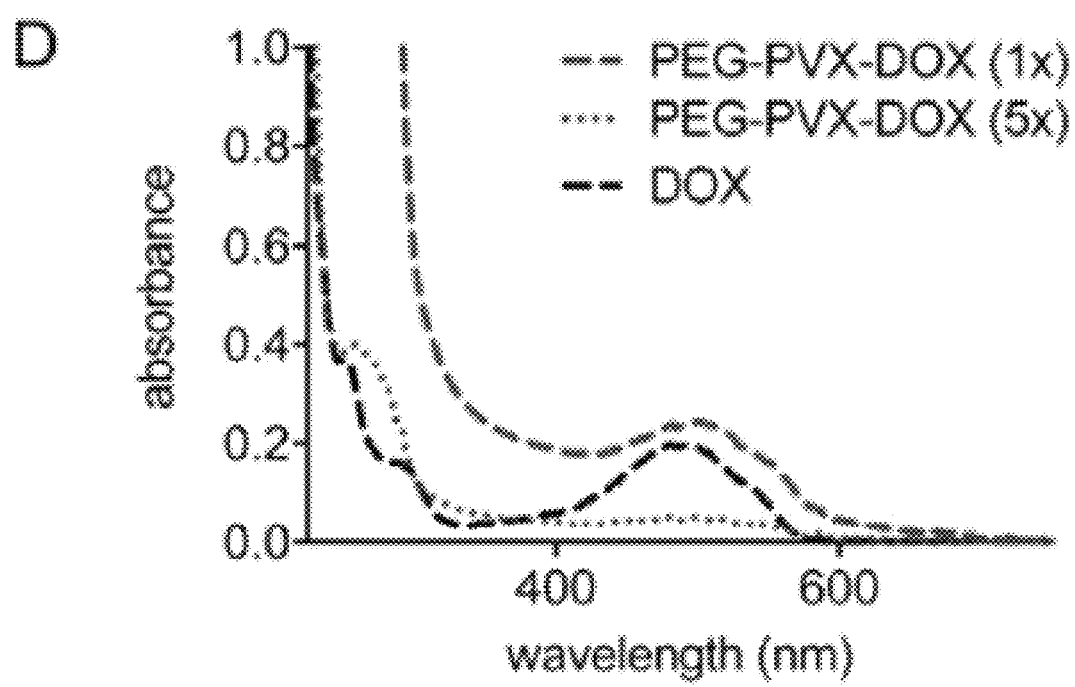
Figs. 14C-D

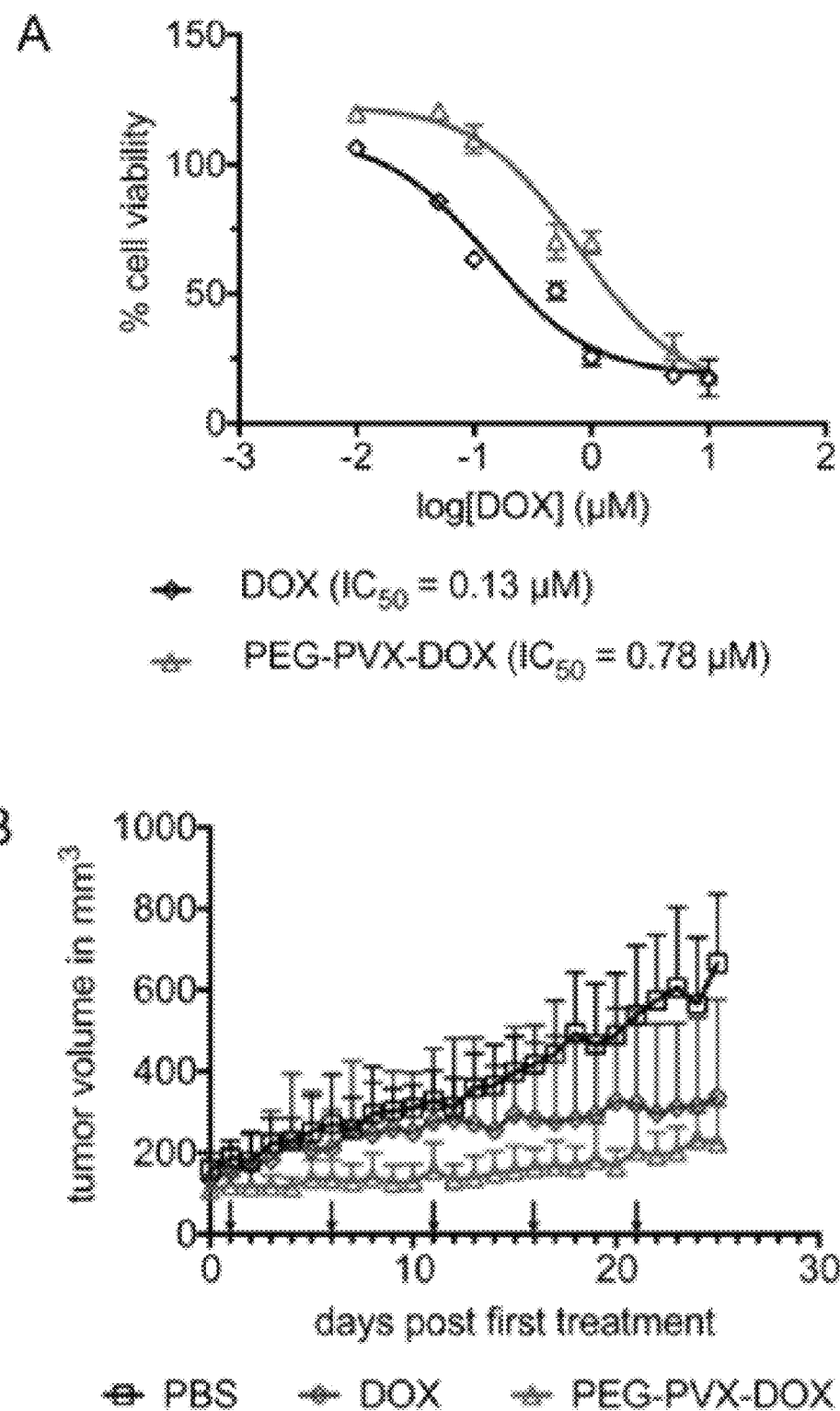
Figs. 15A-B

CANCER IMMUNOTHERAPY USING VIRUS PARTICLES

RELATED APPLICATION

This application claims priority from U.S. Provisional Application No. 62/469,869, filed Mar. 10, 2017, and U.S. patent application Ser. No. 15/589,677, filed May 8, 2017, the subject matter of which are incorporated herein by reference in their entirety.

GOVERNMENT FUNDING

This invention was made with government support under Grant No. CA148052 and EB007509 awarded by The National Institutes of Health. The United States government has certain rights in the invention.

BACKGROUND

Regardless of tissue of origin, metastatic cancers uniformly carry poor prognoses. Conventional chemo- and radiotherapy are largely ineffective for late stage disease. The emerging field of tumor immunology offers new therapeutic options. Novel therapeutics that seek to induce anti-tumor immunity, such as immune checkpoint inhibitors, chimeric antigen receptor cell therapies, and tumor-associated antigen cancer vaccines show promise, but the development of immunotherapy for cancer is in an early stage. Each cancer type is unique but many solid tumors metastasize to the lungs. An option with limited exploration is direct application of immunostimulatory reagents into the suspected metastatic site or an identified tumor. This approach, in situ vaccination, can modulate the local microenvironment and, like therapies such as T cell checkpoint blocking antibodies, can relieve immunosuppression and potentiate anti-tumor immunity against antigens expressed by the tumor.

Research into nanoparticles as cancer therapies has focused on them as a delivery platform: the loading of particles with tumor-associated antigen and immune agonists for the stimulation of anti-tumor immunity, or the loading of particles with pre-existing conventional chemotherapeutic drugs for delivery to tumors as a means to reduce toxicity. Sheen et al., Wiley Interdiscip Rev Nanomed Nanobiotechnol., 6(5):496-505 (2014). However, the tendency of nanoparticles to interact with and to be ingested by innate immune cells gives them potential as immunostimulatory, immunoregulatory and immunostimulatory agents if they modulate the characteristics of the ingesting innate immune population.

Virus-like particles (VLPs) refer to the spontaneous organization of coat proteins into the three dimensional capsid structure of a particular virus. Like active viruses, these particles are in the 20-500 nm size range. VLPs have already been deployed as antigen components of antiviral vaccines against infectious counterpart viruses hepatitis B (Halperin et al., Vaccine, 30(15):2556-63 (2012)) and human papilloma virus (Moreira et al., Hum Vaccin., 7(7):768-75 (2011)). By preventing infection with viruses that cause cancer, vaccines utilizing VLPs are currently contributing to reductions in cancer incidence.

Recent studies have demonstrated that VLP therapeutic efficacy extends beyond the specific antigen array that they carry and that they may possess inherent immunogenic properties that can stimulate immune responses against infectious agents that do not carry any antigen included in the VLP. Rynda-Apple et al., Nanomed., 9(12):1857-68 (2014)). VLPs have shown the ability to induce protective immune responses in the respiratory tract in mouse models of infectious diseases of the lungs. VLP treatment protected mice from bacterial pneumonia caused by methicillin-resistant *Staphylococcus aureus* (MRSA) (Rynda-Apple et al., Am J Pathol., 181(1):196-210 (2012)) and *Coxiella burnetii* (Wiley et al., PLoS ONE., 4(9):e7142 (2009)). VLPs have also been shown to protect mice in various influenza models. Patterson et al., ACS Nano., 7(4):3036-44 (2013); Richert et al., Eur J Immunol., 44(2):397-408 (2014). Protective immunity in these models was associated with recruitment, activation, and increased antigen-processing capabilities, formation of inducible bronchus-associated lymphoid tissue (iBALTs), and stimulation of $CD4^+$ T and B lymphocytes and $CD8^+$ T cells. It is important to note that these studies reported robust induction of both innate and adaptive immunity and that the VLPs utilized were not antigenically related to the infectious agents, yet appeared to exert their therapeutic effect via the inherent immunomodulatory nature of the particles.

SUMMARY

Embodiments described herein relate to methods of treating cancer in a subject in need thereof by administering in situ to cancer of the subject a therapeutically effective amount of a virus or virus-like particle. The virus or virus-like particle can be nonreplicating and noninfectious in the subject to avoid infection of the subject. In some embodiments, the in situ administration of the virus particle can be proximal to a tumor or directly to the tumor site to provide a high local concentration of the virus particle in the tumor microenvironment. The method represents a type of in situ vaccination, in which application of an immunostimulatory reagent directly to the tumor modifies the tumor microenvironment so that the immune system is able to respond to the tumor.

It was found that plant virus and virus-like particles and their unique therapeutic features, originally observed in lung infectious disease models, could be utilized for a new application: treating cancer, such as lung cancer. Primary lung cancer is the second most common cancer in the United States, behind only breast cancer. Additionally, most other majors cancers frequently metastasize to the lung, including breast, bladder, colon, kidney, melanoma, and prostate. Their research focused on melanoma due to its increasing incidence in the US and the poor prognosis for metastatic disease, which currently has a 5-year survival of below 10%. Flaherty et al., N Engl J Med., 363(9):809-19 (2010).

In some embodiments, the virus like particle (VLP) can include eCPMV, which does not carry any nucleic acids or potato virus X (PVX) VLP. These plant viruses can be nonreplicative and can be regarded as safe from a human health and agricultural perspective. In planta production prevents endotoxin contamination that may be a byproduct of other VLP systems derived from *E. coli*. The VLPs are scalable, stable over a range of temperatures (4-60° C.) and solvent:buffer mixtures. In situ vaccination or administration of CPMV or PVX VLPs alone or in combination with a chemotherapeutic in a model of metastatic lung melanoma as well as dermal melanoma and other cancers (breast, colon, ovarian), was found to have striking efficacy in treating the cancer.

The in situ vaccination approach does not rely on the virus-like particles as a vehicle for drug or antigen delivery, but rather on their inherent immunogenicity. This immunogenicity appears to be uniquely potent when the particles are inhaled or when administered through intratumoral administration into dermal tumors or as IP administration when treating disseminated, metaststic ovarian cancer. For treatment of lung tumors, the particles can be intratracheally injected into mice with established lung tumors and this immunostimulatory treatment results in the rejection of those tumors and systemic immunity that prevents growth of distal tumors. The virus-like particles described herein (e.g., CPMV or PVX) alone are able to stimulate systemic anti-tumor immunity. The virus can potentially render the lung microenvironment inhospitable to tumor cell seeding or continued growth.

BRIEF DESCRIPTION OF THE FIGURES

FIGS. 1A and 1B provides bar graphs showing eCPMV nanoparticles are inherently immuonogenic. (A) Bone marrow-derived dendritic cells (BMDCs) exposed to eCPMV produce elevated levels of pro-inflammatory cytokines in vitro. (B) Thioglycollate-elicited primary macrophages also secrete significantly elevated levels of the same panel of cytokines. Both cell types were cultured for 24 hr with 20 μg eCPMV (dark gray bars) and cytokine levels were analyzed using a multiplexed luminex array.

FIG. 2A-2D provides graphs showing eCPMV inhalation induces dramatic changes in immune cell composition and cytokine/chemokine milieu in B16F10 lung tumor-bearing mice. (A) Representative FACS plots pre-gated on live CD45$^+$ cells of non-tumor-bearing mice treated with PBS (top left) or eCPMV (top right) and B16F10 lung tumor-bearing mice treated with PBS (bottom left) or eCPMV (bottom right). B16F10 mice were treated on day 7 post-B16F10 IV injection. Lungs were harvested 24 hr after intratracheal injection of PBS or 100 ug eCPMV. Labeling indicates (i) quiescent neutrophils, (ii) alveolar macrophages, (iii) monocytic MDSCs, (iv) granulocytic MDSCs, (v) tumor-infiltrating neutrophils, and (vi) activated neutrophils. Numbers beside circled groups is % of CD45$^+$ cells. Arrows indicate TINs (blue) and CD11b$^+$ activated neutrophils (red). Gating strategies available in supplemental data. (B) Changes in innate cell subsets induced by eCPMV inhalation are quantified as a percentage of CD45$^+$ cells (top) and total number of cells (bottom) as presented in panel (A). (C) Representative histograms for TINs, activated neutrophils, alveolar macrophages, and monocytic MDSCs indicating uptake of Alexa488-labeled CPMV, class-II, and CD86 activation markers. (D) Lungs of B16F10 lung tumor-bearing mice exhibited elevated levels of pro-inflammatory cytokines and chemoattractants when treated with eCPMV as in panel (A).

FIGS. 3A-3D provide graphs and images showing eCPMV inhalation prevents formation of B16F10 metastatic-like lung tumors. (A) Schematic of experimental design. (B) Photographic images of lungs from eCPMV- and PBS-treated B16F10 tumor-bearing mice on day 21 post-tumor challenge. (C and D) B16F10 lung metastatic-like tumor foci were quantified both by number in (C) or by qRT-PCR assay for melanocyte-specific Tyrp1 mRNA expression in (D).

FIGS. 4A-4C provide graphs showing eCPMV treatment efficacy in B16F10 lung model is immune-mediated. (A) eCPMV inhalation did not significantly affect tumor progression when mice lack 11-12. (B) Treatment efficacy was also abrogated in the absence of Ifn-γ. (C) NOD/scid/I12R-γ$^{-/-}$ mice lacking T, B, and NK cells also failed to respond to eCPMV inhalation therapy FIGS. 5A-5D provide graphs and images showing eCPMV immunotherapy is successful in metastatic breast, flank melanoma, colon, and ovarian carcinoma models. (A) Mice challenged with 4T1 breast tumors and intratracheally injected with PBS rapidly developed (IVIS images) and succumbed (Kaplan-Meier) to metastatic lung tumors beginning on day 24, whereas tumor development was delayed and survival significantly extended in mice receiving intratracheal injection of eCPMV. (B) Mice bearing intradermal flank B16F10 tumors directly injected with eCPMV (arrows indicate treatment days) showed noticeably delayed tumor progression relative to PBS-injected controls and, in half of eCPMV-treated mice, the tumor was eliminated altogether. (C) Mice bearing intradermal flank CT26 colon tumors also responded to direct injection of eCPMV (arrows indicate treatment days) with significantly delayed growth when compared to PBS-injected controls. (D) eCPMV also proved successful as a therapy for ID8-Defb29/Vegf-A ovarian cancer-challenged mice, significantly improving survival when injected IP relative to PBS-injected controls.

FIGS. 6A and 6B provide a timechart (A) and a graph (B) showing eCPMV treatment of dermal B16F10 induces systemic anti-tumor immunity.

FIGS. 7A-D are a schematic and transmission electron micrographs of (A) PVX and (B) CPMV. C+D) Tumor treatment study. Tumors were induced with an intradermal injection of 125,000 cells/mouse. Mice (n=3) were treated with 100 μg of PVX or CPMV (or PBS control) once weekly, starting 8 days post-induction. Arrows indicate injection days; mice were sacrificed when tumor volumes reached 1000 mm3. (C) Tumor growth curves shown as relative tumor volume. (D) Survival rates of treated mice.

FIGS. 8A-E illustrate synthesis and characterization of PVX-DOX. A) Scheme of DOX loading onto PVX. B) Agarose gel electrophoresis of PVX, PVX-DOX, and free DOX under UV light (top) and after Coomassie Blue staining (bottom). C) TEM images of negatively stained PVX-DOX. D) UV/visible spectrum of PVX-DOX. E) Efficacy of PVX-DOX vs. DOX in B16F10 cells after 24 hours exposure (MTT assay).

FIGS. 9A-C illustrate chemo-immunotherapy treatment of B16F10 tumors. Groups (n=6) were treated with PBS, PVX, DOX, PVX-DOX, or PVX+DOX. PVX was administered at a dose of 5 mg kg$^{-1}$, DOX was administered at a dose of 0.065 mg kg$^{-1}$. Injections were repeated every other day until tumors reached >1000 mm3. A) Tumor growth curves shown as relative tumor volume. Statistical significance was detected comparing PVX vs. PVX+DOX. B) Survival rates of treated mice. C) Immunofluorescence imaging of three representative PVX-DOX tumor sections after weekly dosing of PVX-DOX (animals received 2 doses of PVX and were collected when tumors reached >1000 mm$^3$. Tumors treated with PVX-DOX (rows 1-3) were sectioned and stained with DAPI (blue), F4/80 (red), and PVX (green). Scale bar=100 μm.

FIGS. 11(A-D) are a synthesis and characterization of DOX-loaded PVX (PVX-DOX). (A) Scheme of doxorubicin (DOX) loading onto potato virus X (PVX). (B) TEM image of negatively stained PVX-DOX. (C) Agarose gel electrophoresis of PVX (lane 1), PVX-DOX (lane 2), and DOX (lane 3) under UV light (top) and after Coomassie Blue (CB) staining (bottom). (D) UV/visible spectra of PVX-DOX at 1× and 5× dilution vs. DOX (at the equivalent concentration).

FIGS. 12(A-D) illustrate the efficacy of DOX (black line) vs. PVX-DOX (blue line) in a panel of cell lines including (A) A2780 human ovarian cancer, (B) MDA-MB-231 human breast cancer, and (C) HeLa human cervical cancer as determined by MTT assay. Cells were treated by DOX or PVX-DOX corresponding to 0, 0.01, 0.05, 0.1, 0.5, 1, 5, or 10 μM (A2780 and MDA-MB-231) or 0, 0.1, 0.5, 1, 5, 10, 25, or 50 μM (HeLa) in 24 h. (D) IC50 values of DOX vs. PVX-DOX were determined using GraphPad Prism software (DOX vs. PVX-DOX p<0.05).

FIGS. 14(A-D) illustrate (A) schematic of the PEGylated, DOX-loaded PEG-PVX-DOX. (B-D) Characterization of PEG-PVX-DOX. (B) Agarose gel electrophoresis of PVX (lane 1), PEG-PVX-DOX (lane 2), and DOX (lane 3); the gel was imaged under UV light (top) and after Coomassie Blue (CB) stain under white light (bottom). (C) SDS-PAGE of PVX (lane 1), PVX-DOX (lane 2), and PEG-PVX-DOX (lane 3) under UV light (left) and after staining with CB (right) photographed under white light. M: SeeBlue Plus2 Protein standard. Released DOX, PVX coat proteins (CP) and PEGylated PEG-CP are detected. (D) UV/visible spectra of PEG-PVX-DOX at 1× and 5× dilution vs. DOX (at the equivalent concentration).

DETAILED DESCRIPTION

Figure 2A:
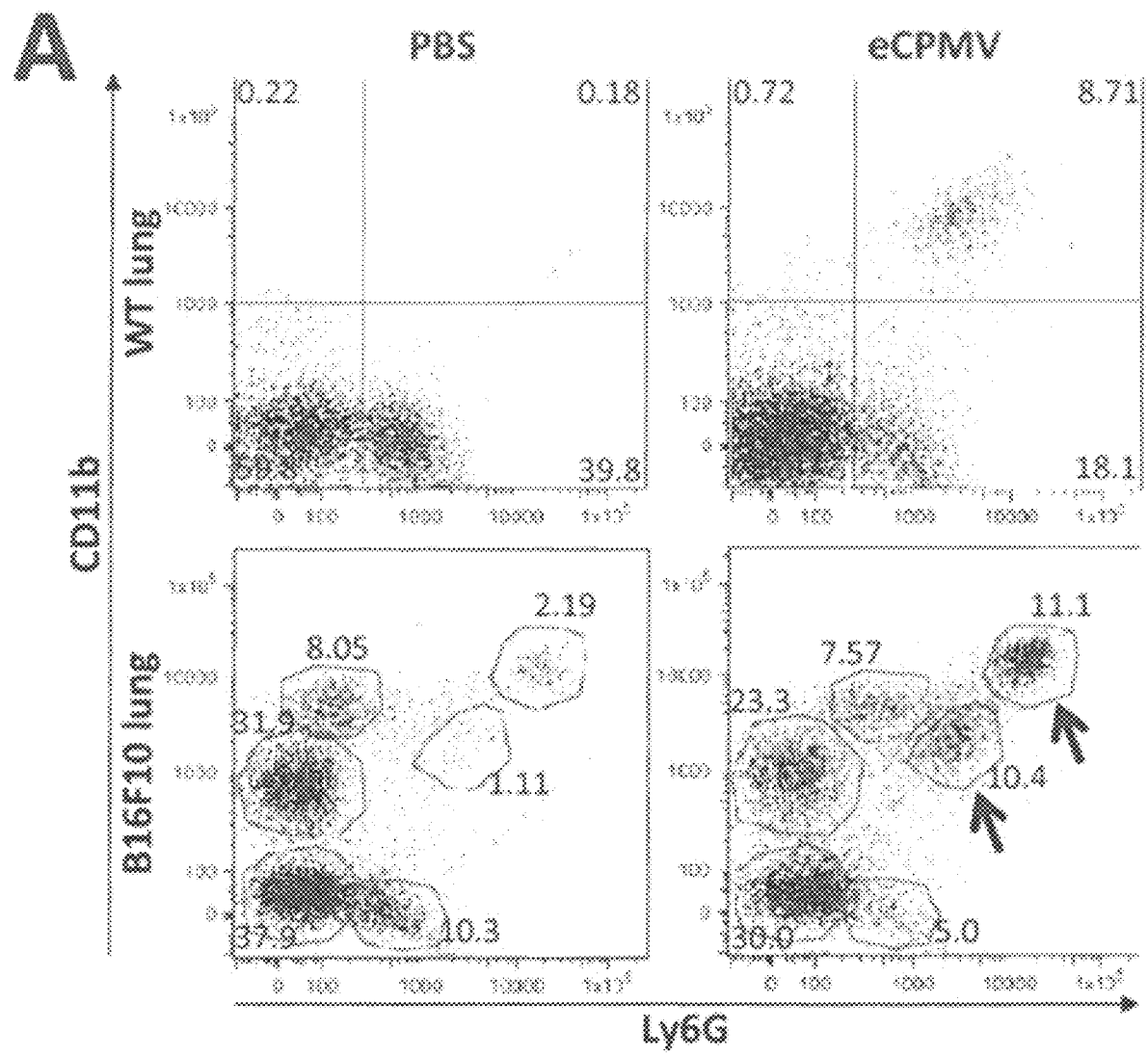

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. A protein may be a receptor or a non-receptor. "Apa" is aminopentanoic acid.

A "nucleic acid" refers to a polynucleotide and includes polyribonucleotides and polydeoxyribonucleotides.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective imaging or treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

Embodiments described herein relate to methods of treating cancer in a subject in need thereof by administering in situ to the cancer a therapeutically effective amount of a virus or virus-like particle to the subject. The virus or virus-like particle can be nonreplicating and noninfectious in the subject to avoid infection of the subject. In some embodiments, the in situ administration of the virus particle can be proximal to a tumor in the subject or directly to the tumor site to provide a high local concentration of the virus particle in the tumor microenvironment.

In some embodiments, virus particles or virus-like particles (VLPs) in which the viral nucleic acid is not present are administered in situ to cancer of the subject. Virus-like particles lacking their nucleic acid are non-replicating and non-infectious regardless of the subject into which they are introduced. An example of virus-like particles is empty Cowpea Mosaic Virus particles. In other embodiments, the virus particles include a nucleic acid within the virus particle. If present, the nucleic acid will typically be the nucleic acid encoding the virus. However, in some embodiments the viral nucleic acid may have been replaced with exogenous nucleic acid. In some embodiments, the nucleic acid is RNA, while in other embodiments the nucleic acid is DNA. A virus particle including nucleic acid will still be nonreplicating and noninfectious when it is introduced into a subject which it cannot infect. For example, plant virus particles will typically be nonreplicating and noninfectious when introduced into an animal subject.

In some embodiments, the virus is a plant virus. However, a bacteriophage or mammalian virus can be used in some embodiments of the invention. When a plant virus is used, in some embodiments the plant virus is a plant picornavirus. A plant picornavirus is a virus belonging to the family Secoaviridae, which together with mammalian picornaviruses belong to the order of the Picornavirales. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily Examples of viruses from the Comovirinae subfamily include Cowpea mosaic virus, Broad bean wilt virus 1, and Tobacco ringspot virus. In a further embodiment, the virus particles are from the Genus comovirus. A preferred example of a comovirus is the cowpea mosaic virus particles.

In other embodiments, the plant virus or plant virus-like particle is an Alphaflexiviridae virus or virus-like particle. The genera comprising the Alphaflexiviridae family include Allexivirus, Botrexvirus, Lolavirus, Mandarivirus, Potexvirus, and Sclerodarnavirus. In further embodiments, the plant virus particle of the vaccine composition is a Potexvirus particle. Examples of Potexvirus include *Allium* virus X, Alstroemeria virus X, Alternanthera mosaic virus, Asparagus virus 3, Bamboo mosaic virus, Cactus virus X, Cassava common mosaic virus, Cassava virus X, Clover yellow mosaic virus, *Commelina* virus X, Cymbidium mosaic virus, Daphne virus X, Foxtail mosaic virus, Hosta virus X, *Hydrangea* ringspot virus, Lagenaria mild mosaic virus, Lettuce virus X, Lily virus X, Malva mosaic virus, Mint virus X, *Narcissus* mosaic virus, Nerine virus X, Opuntia virus X, *Papaya* mosaic virus, Pepino mosaic virus, Phaius virus X, *Plantago asiatica* mosaic virus, *Plantago* severe mottle virus, Plantain virus X, Potato *aucuba* mosaic virus, Potato virus X, Schlumbergera virus X, Strawberry mild yellow edge virus, Tamus red mosaic virus, Tulip virus X, White clover mosaic virus, and Zygocactus virus X. In some embodiments, the plant virus like particle is a Potato virus X virus-like particle.

The virus or virus-like particles can be obtained according to various methods known to those skilled in the art. In embodiments where plant virus particles are used, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

Cancer Treatment by Virus Particle Administration

This application describes a method of treating cancer in a subject in need thereof by administering in situ a therapeutically effective amount of a virus or virus-like particle to the subject. While not intending to be bound by theory, it appears that the virus particles have an anticancer effect as a result of eliciting an immune response to the cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the virus particles are used to treat cancer selected from the group consisting of but not limited to melanoma, breast cancer, colon cancer, lung cancer, and ovarian cancer. In some embodiments, the virus particles are used to treat lung cancer. Inhalation is a preferred method of administering the virus or virus-like particles when treating lung cancer. However, inhaled virus particles are able to treat cancer beyond the lung as a result of their ability to stimulate a systemic immune response. For example, in some embodiments, the virus particles are used to treat metastatic cancer which has spread to one or more sites beyond the initial point where cancer has occurred. In other embodiments, the virus or virus-like particles can be administered proximal to tumors in other tissues.

In some embodiments, the method can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step ablating the cancer includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine 0-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, the step ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanised or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies that can be used together with the virus or virus-like particles of the invention for cancer treatment.

In some embodiments, the anti-cancer agent is co-administered with the virus or virus-like particles. In some embodiments, the anti-cancer agent can be physically coupled to or complexed with the virus or virus-like particles and administered in situ to the cancer. In other embodiments, the anti-cancer agent co-administered separately with the virus or virus-like particles (i.e., is not physically coupled to and/or complexed with the virus or virus-like particles). Advantageously, it was found that co-administering the anti-cancer agent with virus or virus-like particles separately (i.e., where the anti-cancer was not physically coupled to the virus or virus-like particles) allowed each agent to more readily act on its own providing significant therapeutic efficacy with prolonged survival, leading to potent anti-tumor effects.

Cargo Molecules

In some embodiments, the virus particle is loaded with or bonded to a cargo molecule. A variety of different types of cargo molecules can be loaded into or bonded to the virus particles. Cargo molecules that are loaded into the virus particle must be sufficiently small to fit within the virus capsid (i.e., have a size of 10 nm or less for a typical icosohedral capsid). Preferred cargo molecules for the present invention include anticancer agents or antitumor agents. Alternately, rather than being loaded into the virus particle, the cargo molecule can be coupled, bonded, or complexed to or with the virus particle. A cargo molecule can be coupled to a virus particle either directly or indirectly (e.g. via a linker group). In some embodiments, the cargo molecule is directly attached to a functional group capable of reacting with the agent. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can serve to increase the chemical reactivity of a substituent on either the agent or the virus particle, and thus increase the coupling efficiency. A preferred group suitable as a site for attaching cargo molecules to the virus particle is one or more lysine residues present in the viral coat protein.

Dosage and Formulation of Virus Particles

When used in vivo, the virus or virus-like particles administered as a pharmaceutical composition, comprising a mixture, and a pharmaceutically acceptable carrier. The loaded picornavirus may be present in a pharmaceutical composition in an amount from 0.001 to 99.9 wt %, more preferably from about 0.01 to 99 wt %, and even more preferably from 0.1 to 95 wt %.

The virus particles, or pharmaceutical compositions comprising these particles, may be administered by any method designed to provide the desired effect. Administration may occur enterally or parenterally; for example orally, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device.

A preferred method for administering the virus particle to a subject having lung cancer is by inhalation. For example, the virus particles can be administered intratracheally to the lung of the subject. For administration by inhalation, the virus particles are preferably formulated as an aerosol or powder. Various methods for pulmonary delivery of nanoparticles are discussed by Mansour et al., Int J Nanomedicine. 2009; 4:299-319, the disclosure of which is incorporated herein by reference.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Suitable doses can vary widely depending on the therapeutic or imaging agent being used. A typical pharmaceutical composition for intravenous administration would be about 0.1 mg to about 10 g per subject per day. However, in other embodiments, doses from about 1 mg to about 1 g, or from about 10 mg to about 1 g can be used. Single or multiple administrations of the compositions may be administered depending on the dosage and frequency as required and tolerated by the subject. In any event, the administration regime should provide a sufficient quantity of the composition of this invention to effectively treat the subject.

The formulations may be conveniently presented in unit dosage form and may be prepared by any of the methods well known in the art of pharmacy. Preferably, such methods include the step of bringing the virus particles into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect.

One skilled in the art can readily determine an effective amount of virus particles to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the virus particles to be administered can be estimated from the volume of cancer cells to be killed or volume of tumor to which the virus particles are being administered.

Useful dosages of the active agents can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the virus particles vary depending upon many different factors, including means of administration, target site, physiological state of the patient, whether the patient is human or an animal, other medications administered, and whether treatment is prophylactic or therapeutic.

Examples have been included to more clearly describe particular embodiments of the invention. However, there are a wide variety of other embodiments within the scope of the present invention, which should not be limited to the particular examples provided herein.

EXAMPLES

Example 1

In Situ Vaccination with Plant-Derived Virus-Like Nanoparticle Immunotherapy Suppresses Metastatic Cancer Current therapies are often ineffective for metastatic cancer and emerging immunotherapies, while promising, are early in development. In situ vaccination refers to a process in which immunostimulatory reagents applied directly to the tumor modify the immunosuppressive microenvironment so that the immune system is able to effectively respond against the tumors. The inventors hypothesized that treatment of lung tumor-bearing mice with a virus-like nanoparticle could modulate the lung immune environment and prevent the development of B16F10 metastatic-like lesions. This example shows that inhalation of a self-assembling virus-like particle derived from cowpea mosaic virus (CPMV) suppresses the development of tumors in the lungs of mice after intravenous challenge. The disparity in tumor burden between CPMV- and PBS-treated mice was pronounced, and the effect was immune-mediated as it was not seen in Ifn-$\gamma^{-/-}$, Il-12$^{-/-}$, or NOD/scid/Il2R$\gamma^{-/-}$ mice. Efficacy was also lost in the absence of Ly6G$^+$ cells. CPMV nanoparticles were rapidly taken up by granulocytic cells in the tumor microenvironment and resulted in their robust activation and cytokine/chemokine production. CPMV nanoparticles are stable, nontoxic, highly scalable, and modifiable with drugs and antigens. These properties, combined with their inherent immunogenicity and significant efficacy against a poorly immunogenic tumor, present CPMV as an attractive novel immunotherapy against cancer metastatic to the lung. Additionally, CPMV exhibited clear treatment efficacy in various other tumor models including dermal melanoma, metastatic breast, colon, and ovarian cancers. This is the first report of a virus-like nanoparticle being utilized as a cancer immunotherapy with proven therapeutic efficacy.

Materials and Methods eCPMV Production and Characterization eCPMV capsids were produced through agroinfiltration of *Nicotiana benthamiana* plants with a culture of *Agrobacterium tumefaciens* LBA4404 transformed with the binary plasmid pEAQexpress-VP60-24K, which contains genes for the coat protein precursor VP60 and its 24K viral proteinase to cleave it into its mature form. 6 days post infiltration, the leaves were harvested and eCPMV extracted using established procedures. The particle concentration was measured using UV/vis spectroscopy ($\varepsilon_{280}$ nm=1.28 mg$^{-1}$ mL cm$^{-1}$), and particle integrity was determined by transmission electron microscopy and fast protein liquid chromatography.

Mice

C57BL/6J (01055) females were purchased from the National Cancer Institute or The Jackson Laboratory. Il-12p35$^{-/-}$ (002692), Ifn-γ$^{-/-}$ (002287), BALB/c (000651), and NOD/scid/Il2Rγ$^{-/-}$ (005557) female mice were purchased from The Jackson Laboratory. All mouse studies were performed in accordance with the Institutional Animal Care and Use Committee of Dartmouth.

Tumor Models

The B16F10 murine melanoma cell line was obtained from Dr. David Mullins (Geisel School of Medicine at Dartmouth College, Hanover, New Hampshire). 4T1-luciferase murine mammary carcinoma cells were provided by Ashutosh Chilkoti (Duke University, Durham, NC). B16F10, 4T1-luc, and CT26 were cultured in complete media (RPMI supplemented with 10% FBS and penicillin/streptomycin). ID8-Defb29/Vegf-A orthotopic ovarian serous carcinoma cells were cultured in complete media supplemented with sodium-pyruvate as previously described. Lizotte et al., Oncoimmunology, 3:e28926. eCollection 2014. Cells were harvested, washed in phosphate-buffered saline (PBS), and injected in the following manner depending on tumor model: $1.25 \times 10^5$ live cells injected intravenously in 200 µL PBS in the tail vein (B16F10 metastatic lung), $1.25 \times 10^5$ live cells injected intradermally in 30 µL PBS in the right flank (B16F10 flank), $1 \times 10^5$ live cells injected intradermally in 30 µL PBS in the right flank (CT26 flank), $2 \times 10^6$ live cells injected intraperitoneally in 200 µL PBS (ID8-Defb29/Vegf-A peritoneal ovarian). For 4T1-luc tumor challenge, $1 \times 10^5$ live cells were injected in 30 µL of PBS into the left mammary fat pad on day 0 and the tumor was surgically removed on day 16, a day by which it is well-established that the tumor has spontaneously metastasized to the lung. Complete removal of primary 4T1-luc tumors was confirmed by bioluminescent imaging. B16F10 and ID8-Defb29/Vegf-A are syngeneic for the C57BL6J strain, whereas CT26 and 4T1-luc are syngeneic for the BALB/c background.

eCPMV Treatment Scheduling

WT, Il-12$^{-/-}$, Ifn-γ$^{-/-}$, NOD/scid/IL2Rγ$^{-/-}$ and Ly6G-depleted mice challenged intravenously with B16F10 were intubated and intratracheally injected with 100 µg of eCPMV in 50 µL PBS on days 3, 10, and 17 post-tumor challenge. For lung challenge experiments, mice were euthanized on day 21 for quantification of metastatic-like lesions and tyrosinase expression. 4T1-luc-bearing mice were intratracheally injected with 20 µg of eCPMV in 50 µL PBS on day 16 (same day as primary tumor removal) and again on day 23 (day 7 post-tumor removal). B16F10 flank tumors were intratumorally injected with 100 µg eCPMV on day 7 post-tumor challenge once tumors had reached 10 mm$^2$ and again on day 14. CT26 flank tumors were intratumorally injected with 100 µg eCPMV on day 8 post-tumor challenge once they had reached 10 mm$^2$ and again on day 15. Flank tumor diameters were measured every other day and mice were euthanized when tumor diameters reached 200 mm$^2$. ID8-Defb29/Vegf-A mice were injected IP with 100 µg of eCPMV weekly beginning on day 7 post-tumor challenge and euthanized when they reached 35 g due to ascites development.

Antibodies and Flow Cytometry

Anti-mouse antibodies were specific for CD45 (30-F11), MHC-II (M5/114.15.2), CD86 (GL-1), CD11b (M1/70), F4/80 (BM8), and Ly6G (1A8) from Biolegend and CD16/CD32 (93) from eBioscience. WT and B16F10 lung tumor-bearing mice were intratracheally injected with 100 µg Alexa-488-labeled CPMV particles 24 hr prior to euthanization. Lungs were harvested and dissociated into single cell suspension using the Miltenyi mouse lung dissociation kit (cat #130-095-927). Red blood cells were removed using lysis buffer of 150 mM NH4Cl, 10 mM KHCO3, and 0.5 mM EDTA. Flow cytometry was performed on a MACSQuant analyzer (Miltenyi). Data were analyzed using FlowJo software version 8.7.

Tyrosinase mRNA Expression Analysis

Whole lungs were dissociated and total RNA was extracted using the RNeasy kit (Qiagen, 74104). cDNA was synthesized using iScript™ cDNA synthesis kit (Bio-Rad, 170-8891). q-PCR was performed on a CFX96™ Real-Time PCR Detection System (Bio-Rad) using iQ™ SYBR® Green Supermix (Bio-Rad, 170-8882) with primers at a concentration of 0.5 µM. mRNA transcript fold-change was calculated using the ΔΔCT method with all samples normalized to mouse Gapdh.

Cytokine Assay

For in vivo cytokine data, total lung homogenate was harvested from B16F10 lung tumor-bearing mice 24 hr post-inhalation of 100 µg eCPMV particles, which was day 8 post-tumor challenge. For in vitro cytokine results, bone marrow-derived dendritic cells (BMDCs) and thioglycollate-stimulated peritoneal macrophages, both derived from C57BL6 mice, were cultured at $1 \times 10^6$ cells/well in 200 µL complete media in 96-well round-bottomed plates with either 20 µg of eCPMV or PBS. Supernatant was harvested after 24 hr incubation. Cytokines were quantified using mouse 32plex Luminex assay (MPXMCYTO70KPMX32, Millipore).

Cell Depletion

Mice were injected with mAb depleting Ly6G (clone 1A8) that was purchased from Bio-X-Cell (cat #BE0075-1) and administered IP in doses of 500 µg one day prior to eCPMV treatment and then once weekly for the duration of survival experiments. Greater than 95% depletion of target cell populations in the lung was confirmed by flow cytometry.

IVIS Imaging

Mice were injected IP with 150 mg/kg of firefly D-luciferin in PBS (PerkinElmer cat #122796) and allowed to rest for 10 min. Imagining was conducted using the Xenogen VivoVision IVIS Bioluminescent and Fluorescent Imager platform and analyzed with Living Image 4.3.1 software (PerkinElmer).

Statistics

Unless noted otherwise, all experiments were repeated at least 2 times with 4-12 biological replicates and results were similar between repeats. Figures denote statistical significance of p<0.05 as *, p<0.01 as , and p<0.001 as *. A p-value <0.05 was considered to be statistically significant. Data for bar graphs was calculated using unpaired Student's t-test. Error bars represent standard error of the mean from independent samples assayed within the represented experiments. Flank tumor growth curves were analyzed using two-way ANOVA. Survival experiments utilized the log-rank Mantel-Cox test for survival analysis. Statistical analysis was done with GraphPad Prism 4 software.

Results eCPMV Nanoparticles are Inherently Immunogenic

Previously published work with VLPs as treatments for pathogenic infections of the respiratory tract utilized a variety of systems and report varying degrees of immunomodulatory capacity. Additionally, these studies often focused on the immune responses to antigens contained in the VLP and not the inherent immunogenicity of the particles themselves, which has not been definitively shown for VLPs. Bessa et al., Eur J Immunol. 38(1):114-26 (2008). Moreover, it is not known if some VLPs are more stimulatory than others. For these reasons, and the inventors proposed use of eCPMV (eCPMV refers to "empty" cowpea mosaic virus particle devoid of RNA) as a novel immunotherapy, they first sought to determine its inherent immunogenicity. eCPMV VLPs were added to in vitro cultures of bone marrow-derived dendritic cells (BMDCs) and primary macrophages harvested from C57BL6 mice. Twenty-four hours of culture with eCPMV particles induced both BMDCs (FIG. 1A) and macrophages (FIG. 1B) to secrete higher levels of canonical pro-inflammatory cytokines including Il-1β, Il-6, Il-12p40, Ccl3 (MIP1-α), and Tnf-α, leading the inventors to conclude that eCPMV is inherently immunostimulatory.

eCPMV Inhalation Radically Alters the B16F10 Lung Tumor Microenvironment

The immunomodulatory effect of eCPMV inhalation on the lung microenvironment was determined next, both in terms of immune cell composition and changes in cytokine and chemokine levels. Exposure of non-tumor-bearing mouse lungs to eCPMV revealed significant activation of Ly6G$^+$ neutrophils 24 hours after exposure as assessed by their upregulation of the CD11b activation marker (Costantini et al., Int Immunol., 22(10):827-38 (2010)) (FIG. 2A top panels) and CD86 co-stimulatory marker. Alexa488-labeling of the particle allowed for cell tracking, which enabled the inventors to confirm that it is this CD11b$^+$Ly6G$^+$ activated neutrophil subset, specifically, that takes up the eCPMV.

Figure 2B:
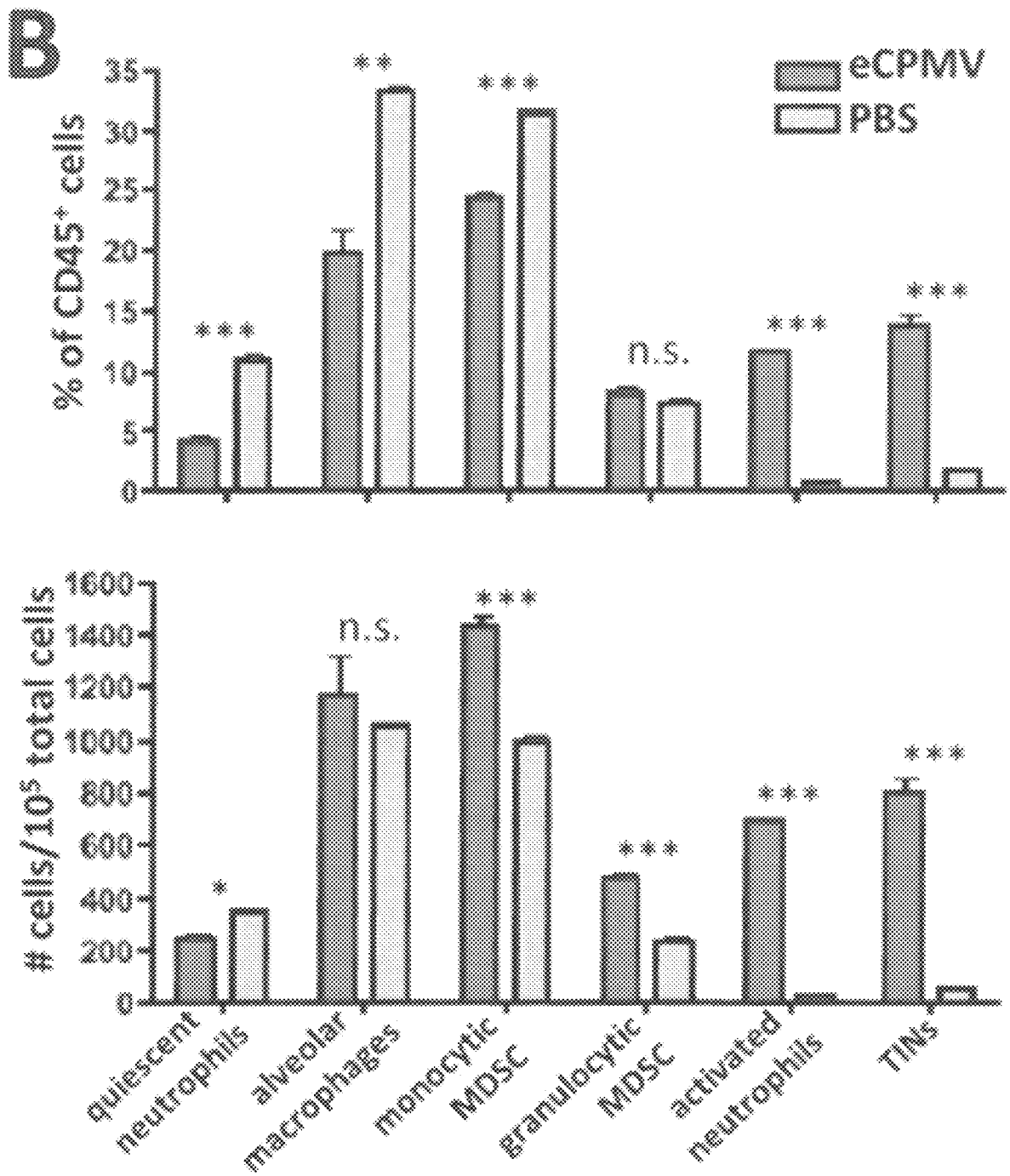

Lungs of mice bearing B16F10 melanoma tumors revealed a more complex immune cell composition. By day 7 the emergence of large populations of immunosuppressive CD11b$^+$Ly6G$^-$F4/80$^{lo}$ class-II$^-$SSC$^{lo}$ monocytic myeloid-derived suppressor cells (MDSCs) and CD11b$^+$Ly6G$^+$F4/80$^-$class-II$^{mid}$SSC$^{hi}$ granulocytic MDSCs (FIG. 2A bottom panels) could be observed. Gabrilovich et al., Nat Rev Immunol., (4):253-68 (2012). The inventors also observed the presence of a small population of CD11b$^+$Ly6G$^+$class-II$^{mid}$CD86$^{hi}$ cells that have been described in the literature as "tumor-infiltrating neutrophils" or "N1 neutrophils" that are known to exert an anti-tumor effect through coordination of adaptive immune responses, production of high levels of pro-inflammatory cytokines, recruitment of T and NK cells, and direct cytotoxicity to tumor cells. Fridlender et al., Cancer Cell. 16(3):183-94 (2009); Mantovani et al., Nat Rev Immunol. (8):519-31 (2011). Inhalation of eCPMV into B16F10-bearing lungs dramatically altered the immune cell composition 24 hours after administration. Significant increases in the tumor-infiltrating neutrophil (TIN) and CD11b$^+$Ly6G$^+$ activated neutrophils populations, as well as a reduction in CD11b$^-$Ly6G$^+$ quiescent neutrophils (FIG. 2A bottom panels, see arrows) were also observed. TIN and activated CD11b$^+$ neutrophil populations increased dramatically both as a percentage of CD45$^+$ cells and also in total number (FIG. 2B). Interestingly, it is these neutrophil subpopulations that took up the vast majority of eCPMV particles, particularly TINs that took up 10-fold more eCPMV than CD11b$^+$ activated neutrophils (FIG. 2C). Monocytic MDSC, quiescent neutrophil, and alveolar macrophage populations did not take up eCPMV, and granulocytic MDSCs displayed uneven uptake. The TIN and activated neutrophil populations also expressed MHC class-II, and the TINs, in particular, displayed high levels of co-stimulatory marker CD86, indicating potential antigen presentation and T cell priming capability. Significant changes were not observed in the numbers of monocytic or granulocytic MDSCs.

Activation of neutrophil populations by eCPMV is consistent with data collected from a multiplexed cytokine/chemokine array performed on whole lung homogenate of B16F10 tumor-bearing lungs treated with eCPMV or PBS (FIG. 2D). Specifically, significant increases in neutrophil chemoattractants GM-CSF, Cxcl1, Cc15, and MIP-1α and significant increases in cytokines and chemokines known to be produced by activated neutrophils such as GM-CSF, 11-9, Cxcl1, Cxcl9, Cxcl10, Cc12, MIP-1α, and MIP-1β were seen. Interestingly, the inventors did not observe significant increases in levels of 11-6 or Tnf-α, which are classical pro-inflammatory cytokines which may be detrimental in the context of lung immunobiology.

eCPMV Inhalation Suppresses B16F10 Metastatic-Like Lung Tumor Development

The inventors next investigated whether the inherent immunogenicity of the eCPMV particle in the lung could induce anti-tumor immunity in the B16F10 intravenous model of aggressive metastatic lung cancer. Indeed, weekly intratracheal injection of 100 μg of eCPMV (FIG. 3A) resulted in significantly reduced tumor burden as assessed by both metastatic-like tumor foci number (FIGS. 3, B and C) and tyrosinase expression (FIG. 3D). Tyrosinase-related protein 1 (Tyrp1) is a melanocyte-specific gene (Zhu et al., Cancer Res., 73(7):2104-16 (2013)) whose expression in the lung is restricted to B16F10 tumor cells, which allows for the quantitative measure of tumor development and serves as a control for the varying sizes of metastatic-like foci.

Anti-Tumor Efficacy of eCPMV Inhalation is Immune-Mediated

The inventors determined whether the immune system was required for treatment efficacy by repeating their experimental design described in FIG. 3 in the following transgenic mice: Il-12$^{-/-}$, Ifn-γ$^{-/-}$, and NOD/scid/IL2Rγ$^{-/-}$. A significant difference in lung tumor burden between eCPMV- and PBS-treated mice was not observed in the absence of Il-12 (FIG. 4A), Ifn-γ (FIG. 4B), or in NSG mice lacking T, B, and NK cells (FIG. 4C).

eCPMV accumulates in and activates neutrophils in the lungs of B16F10 tumor-bearing mice (FIG. 2, A to C). Additionally, significant increases in neutrophil-associated cytokines and chemokines were detected in the mouse lung following eCPMV inhalation (FIG. 2D). Therefore, neutrophils were depleted using a monoclonal antibody to assess the necessity of neutrophils for treatment efficacy. Depletion of neutrophils from the lungs of tumor-bearing mice abrogated the anti-tumor effect that we observed in WT mice (FIG. 4D). This, combined with the lack of efficacy observed in I1-12$^{-/-}$, Ifn-γ$^{-/-}$, and NSG mice leads the inventors to conclude that the anti-tumor effect of eCPMV inhalation on B16F10 development is through immunomodulation of the lung tumor microenvironment and, in particular, requires the presence of the neutrophil compartment.

eCPMV Anti-Tumor Efficacy is not Restricted to the B16F10 Intravenous Lung Model The inventors sought to ascertain whether eCPMV treatment efficacy was restricted to the B16F10 metastatic lung model or if the immunomodulatory anti-tumor effect could transfer to other models. The 4T1 BALB/c syngeneic breast cancer model, which is a transferrable yet truly metastatic model, was first utilized. 4T1 tumors established in the mammary fat pad spontaneously metastasize to the lung by day 16, at which point the primary tumor was surgically removed and eCPMV treatment begun, injecting intratracheally to affect lung tumor development. The 4T1 cells also expressed luciferase, allowing the inventors to track metastatic lung tumor development. Mice treated intratracheally with eCPMV particles had significantly delayed lung tumor onset and significantly extended survival (FIG. 5A). Mice from eCPMV and PBS treatment groups had comparable primary mammary fat pad tumor burden at day of surgical removal. Therefore, differences in tumor development and survival were due to treatment. No mice from either group experienced recurrence of primary mammary fat pad tumors.

To determine whether the eCPMV particle's unambiguous efficacy in B16F10 and 4T1 metastatic lung models was unique to the lung immune environment, its ability to treat dermal tumors was also tested. Both intradermal B16F10 melanoma (FIG. 5B) and CT26 colon (FIG. 5C) tumor growth was significantly delayed following direct injection with eCPMV and, in half of the B16F10 eCPMV-treated mice, resulted in elimination of the tumors altogether after only two treatments (FIG. 5B).

Figure 5D:
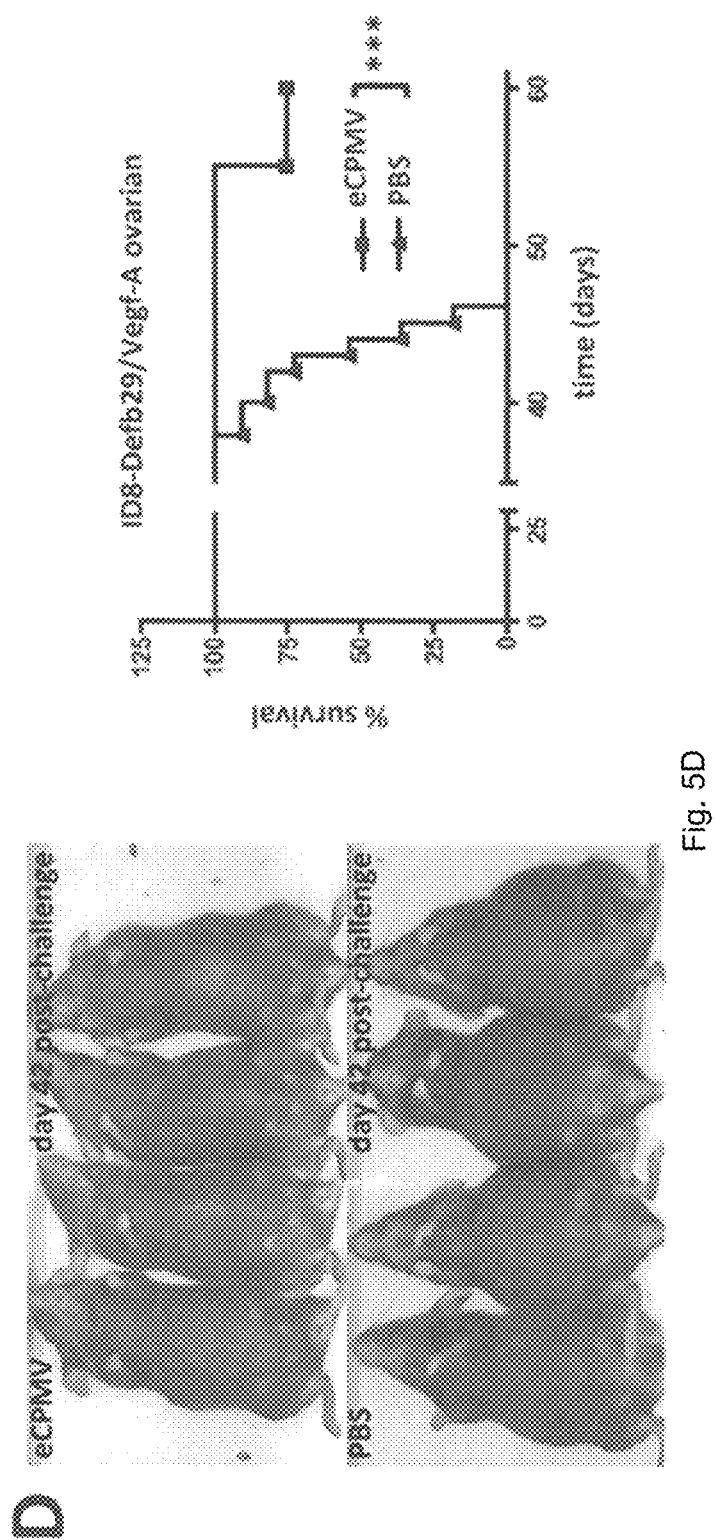

Finally, the therapeutic effect of eCPMV was investigated in a model of disseminated peritoneal serous ovarian carcinoma. Conejo-Garcia et al., Nat Med., (9):950-8 (2004). ID8-Defb29/Vegf-A-challenged mice treated weekly with eCPMV exhibited significantly improved survival relative to PBS-treated controls (FIG. 5D). In fact, mice receiving eCPMV survived longer in comparison than other immunotherapies attempted in this model including a live, attenuated *Listeria monocytogenes* strain (Lizotte et al., Oncoimmunology, 3:e28926. eCollection 2014), avirulent *Toxoplasma gondii* (Baird et al., Cancer Res., 73(13):3842-51 (2013)), combination agonistic CD40 and poly(I:C) (Scarlett et al., Cancer Res., 69(18):7329-37 (2009)), or 11-10 blocking antibody (Hart et al., T Cell Biol., 2:29 (2011)). It is important to note that the anti-tumor effects of eCPMV in the tested models are not attributable to direct tumor cell cytotoxicity, as exposure to high concentrations of the particle in vitro had no effect on cancer cell viability or proliferation. The logical conclusion is that the striking anti-tumor effect induced by eCPMV nanoparticle treatment is fully immune-mediated and translatable to a variety of tumor models across diverse anatomical sites.

eCPMV nanoparticles are immunotherapeutic to a surprisingly high degree and clearly modulate the tumor immune environment. BMDCs and macrophages exposed to the particles robustly secreted select pro-inflammatory cytokines (FIGS. 1A and B). eCPMV particles were produced in plants, then plant contaminants were extracted using polyvinyl-polypyrrolidone, eCPMV isolated through PEG precipitation and sucrose gradient ultracentrifugation, and finally the particles concentrated by ultrapelleting. Purity was checked by UV/Vis absorbance, transmission electron microscopy (TEM), fast protein liquid chromatography (FPLC), and SDS gel electrophoresis. Wen et al., Biomacromolecules, 13(12):3990-4001 (2012). No contaminants were detected during these procedures. Particles were then resuspended in PBS. Additionally, eCPMV is completely devoid of RNA that could stimulate TLR3/7. The inventors therefore conclude that the high immunogenicity of eCPMV is due to the size, shape, or inherent immune recognition of the viral coat protein. This is unlike virus-like or protein cage nanoparticles that are manufactured in *E. coli* or other systems that may contain immunogenic contaminants like endotoxin or viral nucleic acids that are challenging to remove during the purification process.

eCPMV inhalation transforms the lung tumor microenvironment and requires the presence of Ly6G$^+$ neutrophils, a population that is minimally associated with response to tumor immunotherapy. Notably, eCPMV particles appear to specifically target Ly6G$^+$ neutrophils. eCPMV has been shown to bind surface vimentin on cancer cells (Steinmetz et al., Nanomed. 6(2):351-64 (2011)) and some antigen-presenting cells (Gonzalez et al., PLoS ONE. 4(11):e7981 (2009)), although it is not known if this is the mechanism by which lung-resident neutrophils are internalizing the particle, or if surface expression of vimentin is a feature of murine neutrophils. eCPMV appears to target quiescent neutrophils and convert them to an activated CD11b$^+$ phenotype, as well as inducing the recruitment of additional CD11b$^+$ activated neutrophils and CD11b$^+$class-II$^+$CD86$^{hi}$ tumor-infiltrating neutrophils. In fact, these two populations—activated neutrophil and tumor-infiltrating or "N1" neutrophils—are the only innate immune cell populations that significantly change rapidly following eCPMV lung exposure, both dramatically increasing as a percentage of CD45+ cells and in total cell number (FIG. 2B). Neutrophils are viewed canonically as sentinels for microbial infection that quickly engulf and kill bacteria before undergoing apoptosis, yet they have an emerging roll in tumor immunology. Although still controversial, it appears that neutrophils possess phenotypic plasticity analogous to the M1/M2 polarization accepted in macrophage literature. Studies have shown infiltration of an immunosuppressive, pro-angiogenic "tumor-associated neutrophil" population in B16F10 metastatic lung, human liver cancer, sarcoma, and lung adenocarcinoma models that is correlated with enhanced tumor progression. Alternatively, depletion of tumor-resident immunosuppressive neutrophils, conversion of them to a pro-inflammatory phenotype, or recruitment of activated neutrophils to infiltrate the tumor microenvironment is associated with therapeutic efficacy. Activated neutrophils can directly kill tumor cells via release of reactive oxygen intermediates (ROI), prime CD4$^+$ T cells and polarize them to a Th1 phenotype, cross-prime CD8$^+$ T cells, and modulate NK cell survival, proliferation, cytotoxic activity and IFN-γ production. Activated neutrophils can also produce Cxcr3 ligands Cxcl9 and Cxcl10 that can recruit CD4$^+$ and CD8$^+$ T cells that are correlated with anti-tumor immunotherapeutic efficacy in melanoma models. The data showing increases in immunostimulatory neutrophil populations (FIG. 2B) agrees with the cytokine data (FIG. 2D), in which increases in neutrophil chemoattractants GM-CSF, Cxcl1, Cc15, and MIP-1α and cytokines and chemokines known to be produced by neutrophils were observed, including GM-CSF, I1-1β, I1-9, Cxcl1, Cxcl9, Cxcl10, Cc12, MIP-1α, and MIP-1β. This data in turn agrees with the in vivo tumor progression data showing that neutrophils are required for eCPMV anti-tumor efficacy. Interestingly, although many cytokine and chemokine levels were elevated to a statistically significant degree following eCPMV treatment, changes were modest when compared to the dramatic differences in actual tumor burden (FIG. 3, B to D). Moreover, increases in pro-inflammatory cytokines Tnf-α or Il-6 that are known to cause tissue damage when upregulated in the lung were not observed. It appears, therefore, that eCPMV treatment of lung tumors is effective without eliciting the kind of inflammatory cytokine response that could cause acute lung injury.

eCPMV inhalation exhibited remarkable efficacy as a monotherapy (FIG. 3) that is very clearly immune-mediated (FIG. 4). This is novel because the eCPMV particle does not directly kill tumor cells or share any antigenic overlap with B16F10 tumors, but induces an anti-tumor response that requires Th1-associated cytokines Il-12 (FIG. 4A) and Ifn-γ (FIG. 4B), adaptive immunity (FIG. 4C), and neutrophils (FIG. 4D). This suggests that the inherent immunogenicity of eCPMV, when introduced into the lung, disrupts the tolerogenic nature of the tumor microenvironment; in essence, removing the brakes on a pre-existing anti-tumor immune response that is suppressed, or allowing a de novo anti-tumor response to develop.

This work also shows that eCPMV anti-tumor efficacy in the intravenous B16F10 metastatic lung model is not an artifact of the C57BL6 mouse strain or the B16F10 model, as eCPMV therapy works equally impressively in flank B16F10, ovarian carcinoma, and two BALB/c models of metastatic breast and colon cancer (FIG. 5). Constitutive luciferase expression in 4T1 breast carcinoma cells and intradermal challenges of B16F10 and CT26 allowed us to measure tumor progression quantitatively in a manner not feasible in the B16F10 lung model. It is in these models that we observed a potent and immediate anti-tumor effect that significantly delayed tumor progression and, in the cases of the B16F10 and CT26 intradermal tumors, induced rapid involution of established tumors and formation of necrotic centers (FIGS. 5, B and C) that remained confined to within the margins of the tumors and did not appear to affect surrounding tissue. Such early responses to eCPMV—day 3 post-intratumoral injection—would indicate that eCPMV particles are inducing innate immune cell-mediated anti-tumor responses. The eCPMV nanoparticle, alone, is immunogenic and highly effective as a monotherapy. However, it can also serve as a nanocarrier for tumor antigens, drugs, or immune adjuvants, opening up the exciting possibilty that eCPMV can be modified to deliver a payload that further augments and improves its immunotherapeutic efficacy.

Example 2 eCPMV Treatment of Dermal B16F10 is Inducing Systemic Anti-Tumor Immunity

As shown in FIG. 6, the inventors established dermal melanoma tumors and injected the eCPMV particles directly into them (100 μg/injection, arrows indicate injection days). In half of the mice this results in complete disappearance of the tumors. In the cured mice, we then waited 4 weeks and re-challenged with the same tumor cells, but we injected tumor cells on the opposite flank. Most of those mice did not develop secondary tumors. To clarify: primary tumors were directly injected with particles, whereas mice bearing secondary tumors received no treatment. They had to rely on systemic anti-tumor immune memory alone. The eCPMV was applied locally in the first tumors, but induced systemic immunity. "Re-challenge" mice where those that previously had B16F10 dermal tumors that were direct-injected and that shrank and disappeared.

Example 3

Using a plant virus-based nanotechnology, we demonstrated that virus like particles (VLPs) from the icosahedral virus cowpea mosaic virus (CPMV, 30 nm in diameter) stimulate a potent anti-tumor immune response when applied as an in situ vaccine. Efficacy was demonstrated in mouse models of melanoma, breast cancer, ovarian cancer, and colon cancer. Data indicate that the effect is systemic and durable, resulting in immune-memory and protecting subjects from recurrence. While the underlying mechanism has not been elucidated in depth, initial studies, in which VLPs were inhaled into the lungs of mice bearing B16F10 lung tumors, revealed a sub-population of lung antigen presenting cells (APC) that are MHC class II+CD11b+ Ly6G+ neutrophils that ingest VLPs and activate following VLP exposure. Further, the increase in this neutrophil population is accompanied by a decrease of myeloid-derived suppressor cells (MDSCs) that mediate immune-suppression in the tumor microenvironment. Here we set out to investigate the use of plant viruses as in situ vaccines and their combination with chemotherapy regimes.

Recent clinical and preclinical research indicates that the combination of chemo- and immunotherapies can be beneficial because the therapy regimes can synergize to potentiate the therapy and improve patient outcomes. For chemo-immuno combination treatment, the use of the anthracycline doxorubicin (DOX) could be a particularly powerful approach, because DOX itself induces immunogenic cell death that elicits an antitumor immune response. The immune response is induced by calreticulin exposure on the surface of dying cells, which facilitates tumor cell phagocytosis by dendritic cells resulting in tumor antigen presentation. Furthermore, doxorubicin-killed tumor cells recruit intratumoral CD11c+CD11b+Ly6Chi myeloid cells, which present tumor antigens to T lymphocytes; therefore, the combination of doxorubicin with tumor vaccines or immunotherapies can synergize and potentiate the overall efficacy.

Example 4

In this example, we set out to address the following questions:
  i) whether the flexuous particles formed by the potato virus X (PVX) would stimulate an anti-tumor response when used as in situ vaccine?
  ii) whether the combination of VLP-based in situ vaccine with DOX chemotherapy would potentiate therapeutic efficacy; specifically we asked whether the formulation as combinatorial nanoparticle where DOX is bound and delivered by PVX (PVX-DOX) or the co-administration of the therapeutic regimens (PVX+DOX) would be the most effective treatment strategy?

All studies were performed using a mouse model of melanoma.

Methods

PVX and CPMV Production

PVX was propagated in *Nicotiana benthamiana* plants and purified as previously reported. CPMV was propagated in *Vigna unguiculata* plants and purified as previously reported.

Synthesis of PVX-DOX

PVX (2 mg mL-1 in 0.1 M potassium phosphate buffer (KP), pH 7.0) was incubated with a 5,000 molar excess of doxorubicin (DOX) at a 10% (v/v) final concentration of DMSO for 5 days at room temperature, with agitation. PVX-DOX was purified twice over a 30% (w/v) sucrose cushion using ultracentrifugation (212,000×g for 3 h at 4° C.) and resuspended overnight in 0.1 M KP, pH 7.0. PVX-DOX filaments were analyzed using UV/visible spectroscopy, transmission electron microscopy, and agarose gel electrophoresis.

UV/Visible Spectroscopy

The number of DOX per PVX filament was determined by UV/visible spectroscopy, using the NanoDrop 2000 spectrophotometer. DOX loading was determined using the Beer-Lambert law and DOX (11,500 M-1 cm-1 at 495 nm) and PVX (2.97 mL mg-1 cm-1 at 260 nm) extinction coefficients.

Transmission Electron Microscopy (TEM)

TEM imaging was performed after DOX loading to confirm integrity of PVX-DOX filaments. PVX-DOX samples (0.1 mg mL$^{-1}$, in dH$_2$O) were placed on carbon-coated copper grids and negatively stained with 0.2% (w/v) uranyl acetate. Grids were imaged using a Zeiss Libra 200FE transmission electron microscope, operated at 200 kV.

Agarose Gel Electrophoresis

To confirm DOX attachment, PVX-DOX filaments were run in a 0.8% (w/v) agarose gel (in TBE). PVX-DOX and corresponding amounts of free DOX or PVX alone were loaded with 6× agarose loading dye. Samples were run at 100 V for 30 min in TBE. Gels were visualized under UV light and after staining with 0.25% (w/v) Coomassie blue.

Cell Culture and Cell Viability Assay

B16F10 cells (ATCC) were cultured in Dulbecco's modified Eagle's media (DMEM, Life Technologies), supplemented with 10% (v/v) fetal bovine serum (FBS, Atlanta Biologicals) and 1% (v/v) penicillin-streptomycin (penstrep, Life Technologies). Cells were maintained at 37° C., 5% $CO_2$. Confluent cells were removed with 0.05% (w/v) trypsin-EDTA (Life Technologies), seeded at 2×10$^3$ cells/100 μL/well in 96-well plates, and grown overnight at 37° C., 5% $CO_2$. The next day, cells were washed 2 times with PBS and incubated with free DOX or PVX-DOX corresponding to 0, 0.01, 0.05, 0.1, 0.5, 1, 5, or 10 μM DOX for 24 h, in triplicate. A PVX only control corresponded to the amount of PVX in the highest PVX-DOX sample. Following incubation, cells were washed 2 times to remove unbound DOX or particles. Fresh medium (100 μL) was added and cells were returned to the 21 incubator for 48 h. Cell viability was assessed using an MTT proliferation assay (ATCC); the procedure was as the manufacturer suggested.

Animal Studies

All experiments were conducted in accordance with Case Western Reserve University's Institutional Animal Care and Use Committee. C57BL/6J male mice (Jackson) were used. B16F10 tumors were induced intradermally into the right flank of C57BL/6J mice (1.25×10$^5$ cells/50 μL media). Animals were monitored and tumor volume was calculated as V=0.5×a×b2, where a=width of the tumor and b=length of the tumor. Animals were sacrificed when tumor volume reached >1000 mm$^3$. Treatment schedule: Eight days post-tumor induction (day 0), mice were randomly assigned to the following groups (n=3): PBS, PVX, or CPMV. Mice were treated intratumorally (20 μL), every 7 days, with 5 mg kg-1 PVX or CPMV. Mice were sacrificed when tumors reached a volume >1000 mm$^3$. For chemo-immunotherapy combination therapy, mice were randomly assigned to the following groups (n=6): PBS, PVX, DOX, conjugated PVX-DOX, or PVX+DOX mixtures. PVX+DOX samples were prepared less than 30 min before injections and are considered not bound to each other. Mice were treated intratumorally (20 μL), every other day, with 5 mg kg$^{-1}$ PVX or PVX-DOX or the corresponding dose of DOX (~0.065 mg kg-1). Mice were sacrificed when tumors reached a volume >1000 mm$^3$.

Immunostaining

When tumor reached volumes <100 mm$^3$, mice were randomly assigned to the following groups (n=3): PBS or PVX-DOX. Mice were treated intratumorally (20 μL), every 7 days, with 5 mg kg-1 PVX-DOX. Mice were sacrificed when tumors reached a volume >1000 mm$^3$ tumors were collected for analysis. Tumors were frozen in optimal cutting temperature compound (Fisher). Frozen tumors were cut into 12 μm sections. Sections were fixed in 95% (v/v) ethanol for 20 minutes on ice. Following fixation, tumor sections were permeabilized with 22 0.2% (v/v) Triton X-100 in PBS for 2 min at room temperature for visualization of intracellular markers. Then, tumor sections were blocked in 10% (v/v) GS/PBS for 60 min at room temperature. PVX and F4/80 were stained using rabbit anti-PVX antibody (1:250 in 1% (v/v) GS/PBS) and rat anti-mouse F4/80 (1:250 in 1% (v/v) GS/PBS) for 1-2 h at room temperature. Primary antibodies were detected using secondary antibody staining: AlexaFluor488-labeled goat-anti-rabbit antibody (1:500 in 1% (v/v) GS/PBS) and AlexaFluor555-labeled goat-anti-rat antibody (1:500 in 1% (v/v) GS/PBS) for 60 min at room temperature. Tumor sections were washed 3 times with PBS in between each step. Following the final wash, coverslips were mounted using Fluoroshield with DAPI. Slides were imaged on a Zeiss Axio Observer Z1 motorized FL inverted microscope. Fluorescence intensity was analyzed using ImageJ 1.47d.

Luminex Assay

Intradermal melanomas were induced in C57BL/6J male mice (Jackson) as described above. Eight days post-tumor induction (day 0), mice were randomly assigned to the following groups (n=4): PBS, PVX, PVX-DOX, or PVX+DOX. Mice were treated intratumorally (20 μL) once and tumors were harvested at 24 h.p.i. Tumors were weighed and homogenized in T-PER™Buffer (ThermoFisher) at 1 mL of buffer/100 mg of tissue. TPER™Buffer was supplemented with cOmplete™ Protease Inhibitor Cocktail tablets (Roche) at one tablet per 8 mL of Buffer. After homogenization, homogenizer was rinsed with 0.5 mL HBSS (ThermoFisher) and added to the homogenate. Homogenate was centrifuged at 9,000×g for 10 minutes at 2-8° C. Supernatants were frozen and kept at −80° C. until analyses. Millipore Milliplex MAP mouse 32-plex was run at the CRWU Bioanalyte Core.

Results

PVX is a filamentous plant virus, measuring 515×13 nm, and is comprised of 1270 identical coat proteins. While different in its physical nature compared to the 30 nm-sized icosahedrons formed by CPMV, PVX and PapMV share similar organization of the nucleoproteins arranged as flexuous soft matter filaments. To test whether PVX would stimulate an anti-tumor response when used as an in situ vaccine, we used the B16F10 melanoma model. B16F10 is a highly aggressive and poorly immunogenic tumor model used extensively for immunotherapy studies; it also has served as a model for the evaluation of the immunotherapeutic potential of virus-based therapies. Its low immunogenicity makes it an attractive platform to investigate new immunostimulatory therapies. B16F10 isografts were induced intradermally on the right flank of C57BL/6J mice. Eight days post-induction (tumor starting volume <100 mm³), mice were randomized (n=3) and treated weekly intratumorally with PBS or 100 μg of PVX or CPMV. Tumor volumes were measured daily and mice were sacrificed when tumors reached >1000 mm³. Treatment with CPMV or PVX alone significantly slowed tumor growth rate and extended survival time compared to PBS (FIG. 7), but there was no significant difference between CPMV and PVX treatment. These data indicate that PVX, like CPMV, can stimulate an anti-tumor response when used as an in situ vaccine.

Having established that PVX in situ vaccination slows tumor growth, we went ahead with a chemo-immuno combination therapy approach. We hypothesized that the combination of chemotherapy delivery, either co-administered (as physical mixture, PVX+DOX) or co-delivered (as complexed version, PVX-DOX), would enhance the anti-tumor effect. The underlying idea was that the chemotherapy would debulk the tumor to provide a burst of tumor antigens in the context of immunogenic cell death. This fosters specific immune recognition and response to those antigens; in turn, VLP-mediated immune-stimulation would further augment anti-tumor immunity and induce memory to protect from outgrowth of metastases and recurrence of the disease.

Figure 8A:
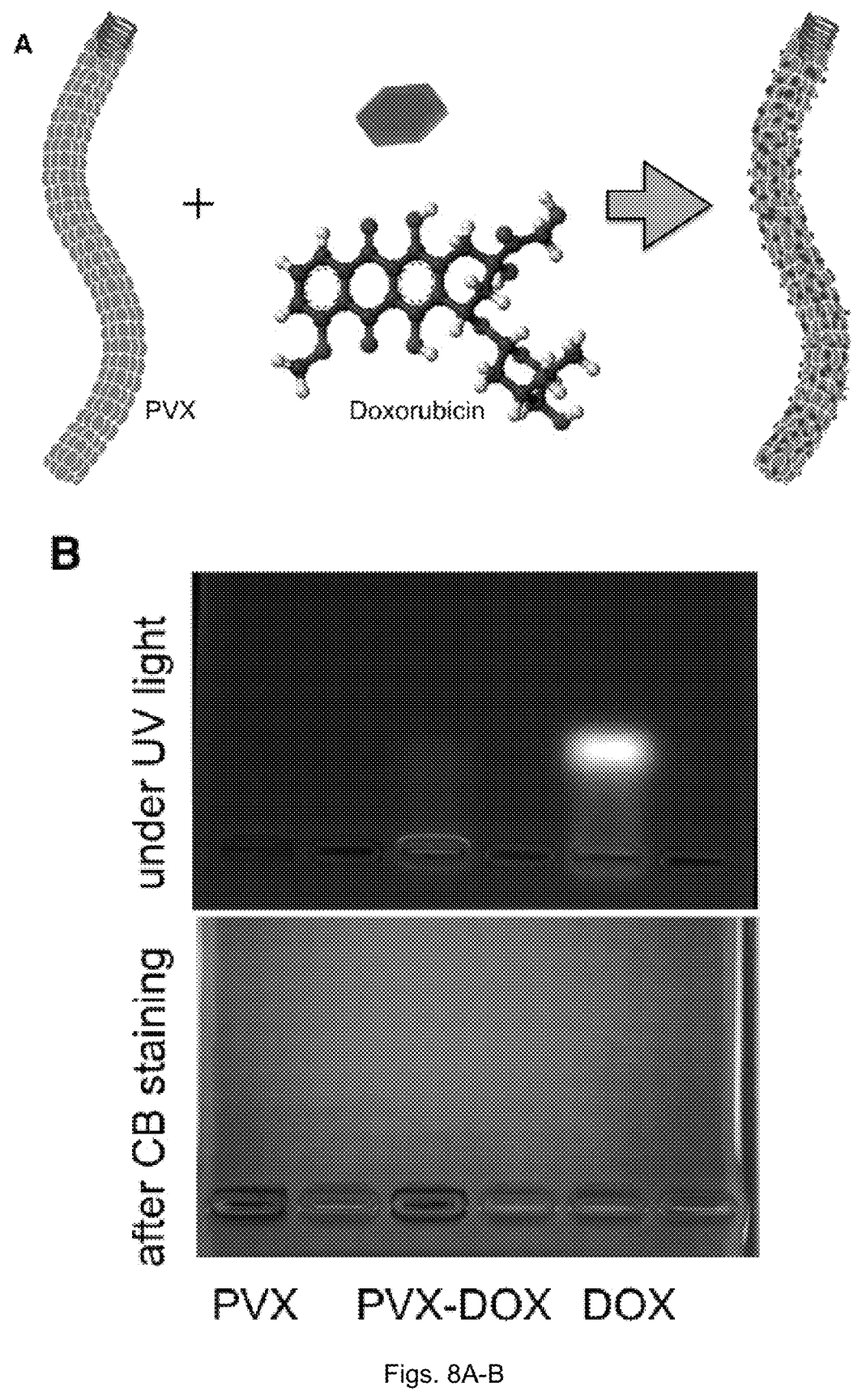

To obtain the PVX-DOX complex (FIG. 8A), purified PVX was loaded with DOX by incubating a 5,000 molar excess of DOX with PVX for 5 days; excess DOX was removed by ultracentrifugation. Incubation criteria were optimized: increasing molar excess of DOX resulted in extensive aggregation and further increasing incubation time did not increase loading capacity (data not shown). The PVX-DOX complex was characterized by agarose gel electrophoresis, UV/visible spectroscopy, and transmission electron microscopy (TEM) (FIGS. 8B-D). TEM imaging confirmed particle integrity following DOX loading. The PVX-DOX formulation stability was confirmed after 1 month of storage at 4° C.; DOX release was not apparent and the particles remained intact (data not shown). UV/visible spectroscopy was used to determine the number of DOX attached per PVX. The Beer-Lambert law, in conjunction with PVX- and DOXspecific extinction coefficients, was used to determine the concentrations of both PVX and DOX in solution. The ratio of DOX to PVX concentration was then used to determine DOX loading. Each PVX was loaded with ~850 DOX per PVX. Agarose gel electrophoresis analysis indicated that DOX was indeed associated with PVX and not free in solution, as free DOX was not detectable in the PVX-DOX sample. The association of DOX with PVX may be explained based on hydrophobic interactions and π-π stacking of the planar drug molecules and polar amino acids.

Figure 8E:
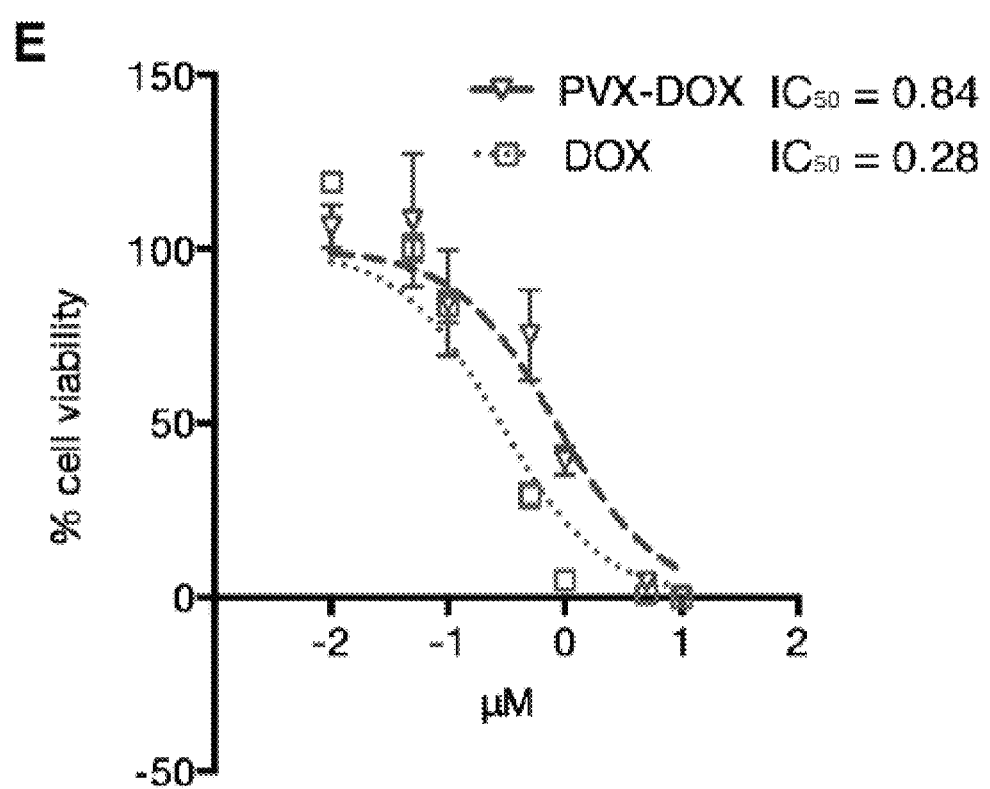

Efficacy of the PVX-DOX complex was confirmed using B16F10 melanoma cells (FIG. 8E). DOX conjugated to PVX maintained cell killing ability, although with decreased efficacy resulting in an $IC_{50}$ value of 0.84 μM versus 0.28 μM for free DOX. Similar trends have been reported with synthetic and virus-based nanoparticles for DOX delivery. The reduced efficacy may be explained by reduced cell uptake and required endolysosomal processing when DOX is delivered by nanoparticles.

To test the hypothesis that a combination chemo-immunotherapy would potentiate the efficacy of PVX alone, DOX-loaded PVX (PVX-DOX) and PVX+DOX combinations were tested in the B16F10 murine melanoma model. The combination of PVX+DOX served to test whether merely the combination of the therapies or the co-delivery (PVX-DOX) would enhance the overall efficacy. PVX+DOX was combined less than 30 min before injection to ensure that the two therapies did not have time to interact. PBS, PVX alone, and free DOX were used as controls. When tumors were <100 mm3, mice were treated every other day intratumorally with PVX-DOX, PVX+DOX, or corresponding controls (n=6). Tumor volumes were measured daily and mice were sacrificed when tumors reached >1000 mm³. PVX was administered at 5 mg kg⁻¹ (corresponding to a dose of 0.065 mg kg-1 DOX). Clinically, doxorubicin is administered at doses of 1-10 mg kg⁻¹, intravenously. If 1-10% of the injected dose reaches the tumor site, the resulting intratumoral dose would equate to 0.01-1 mg kg⁻¹; thus our intratumoral dose is within a clinically relevant range of DOX.

Figure 9C:
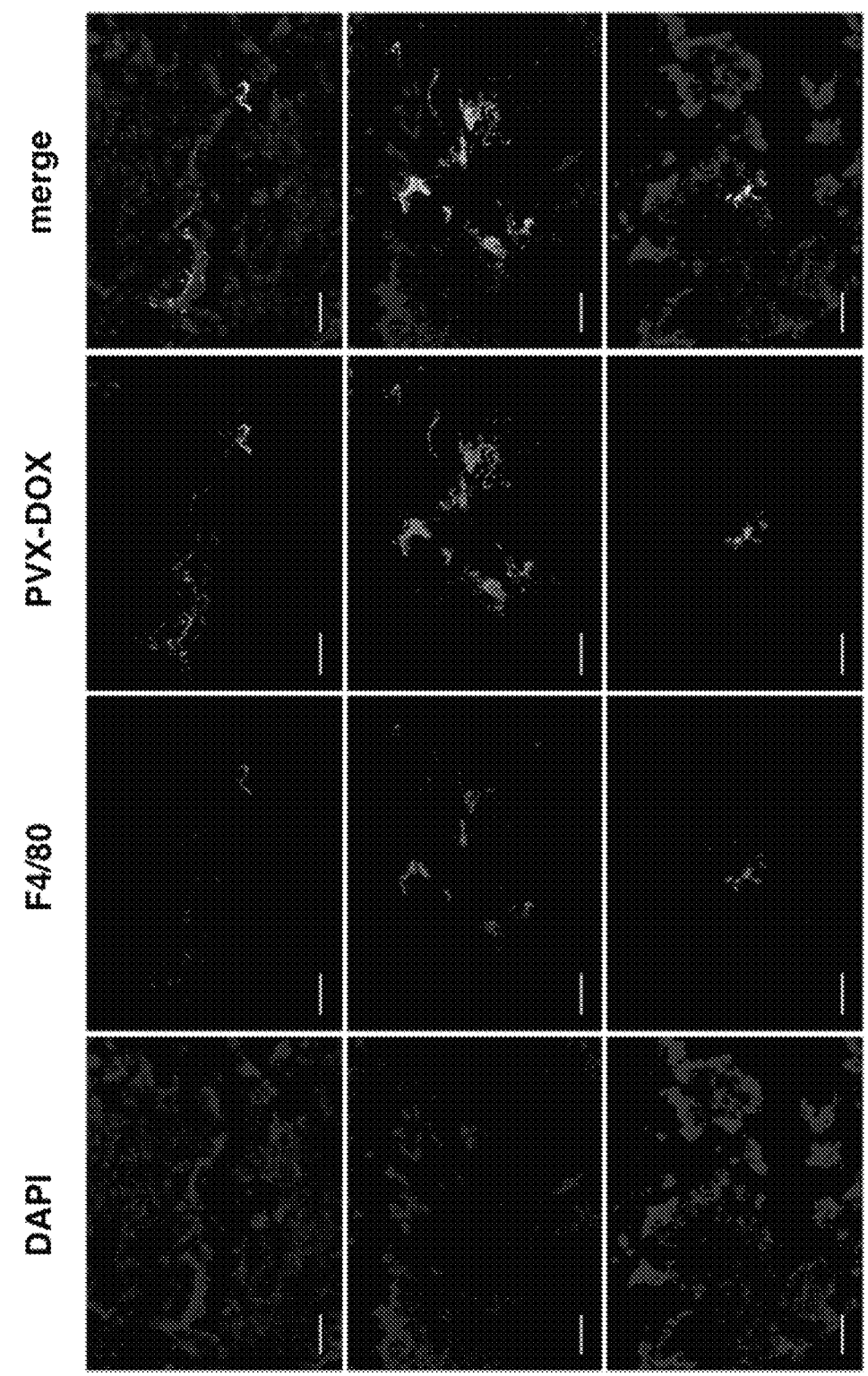

While there was no statistical difference in tumor growth rate or survival time between PVX-DOX complex versus PVX or DOX alone, PVX+DOX did significantly slow tumor growth rate versus PVX and DOX alone (FIGS. 9A+B). Thus, the data indicate that the combination of DOX chemotherapy and PVX immunotherapy indeed potentiates efficacy, however the formulation as a combined nanoparticle, PVX-DOX, did not improve the treatment. The lack of statistically significant enhancement of efficacy of the PVX-DOX complex versus immuno- or chemo-monotherapy may be explained by the fact that the therapies synergize best when they act on their own. DOX targets replicating cancer cells to induce cell death, and PVX likely associated with immune cells to stimulate an anti-tumor effect—most likely through activation of signaling cascades through pathogen-associated molecular pattern (PAMP) receptors and other danger signals. Indeed, we found that PVX was co-localized with F4/80+ macrophages within the tumor tissue (FIG. 9C), which may cause killing of immune cells rather than cancer cells; even if the nanoparticles do not exhibit cytotoxic effect on the immune cell population, the sequestration of PVX-DOX in the immune cells would lower the anti-tumor efficacy of the complex.

Figure 10:
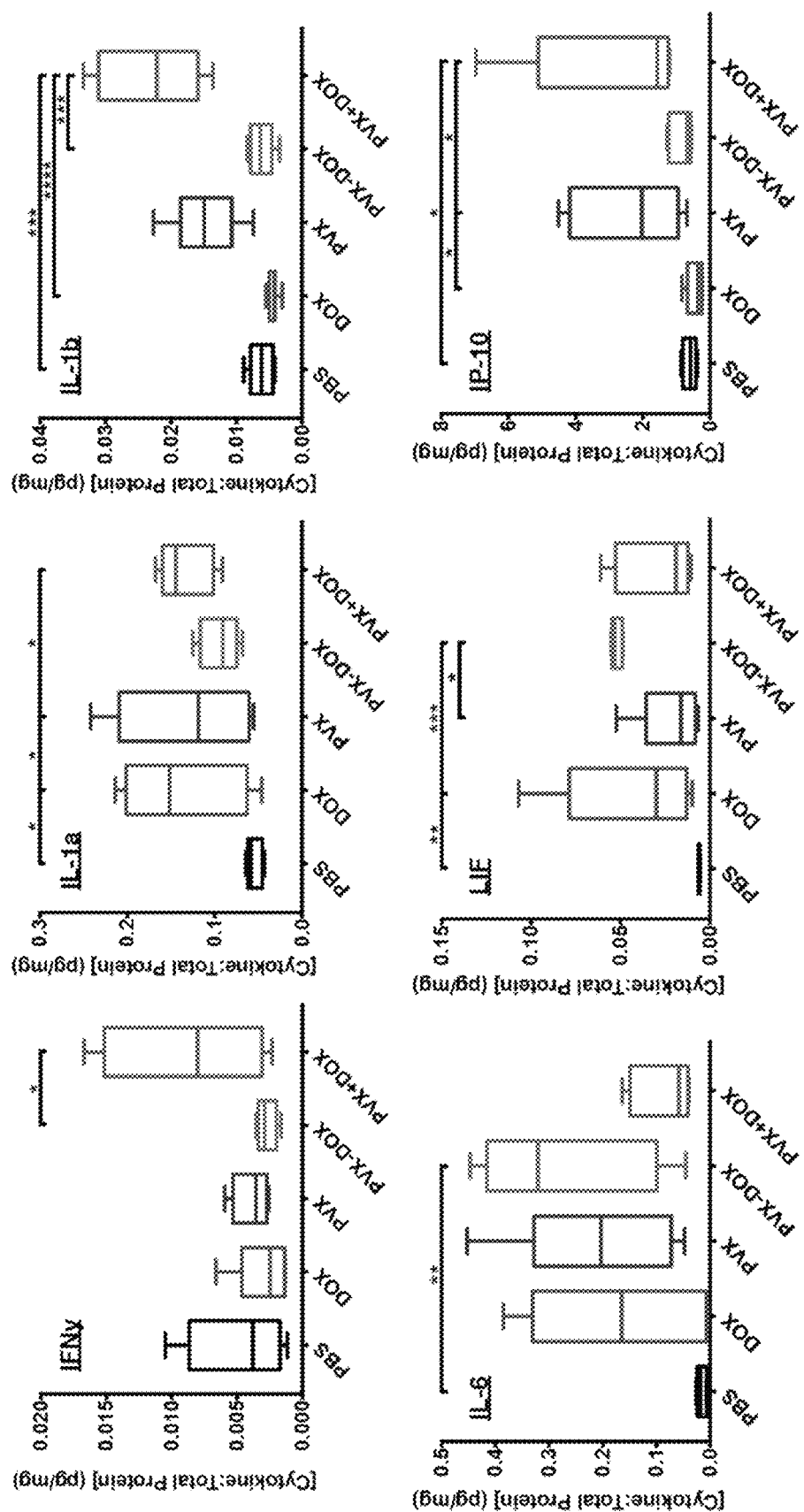
FIG. 10 illustrates Luminex Multiplex Cytokine/Chemokine profiles. Groups (n=4) were treated with PBS, PVX, DOX, PVX-DOX, or PVX+DOX. PVX was administered at a dose of 5 mg kg$^{-1}$, DOX was administered at a dose of 0.065 mg kg$^{-1}$. After one injection, tumors were harvested at 24 hours post injection for analysis. Data shown as ratio of cytokine concentration:total protein (or cytokine per total protein in pg/mg). *=<0.05, =<0.01, *=<0.001, ****=<0.0001).
Figure 10:
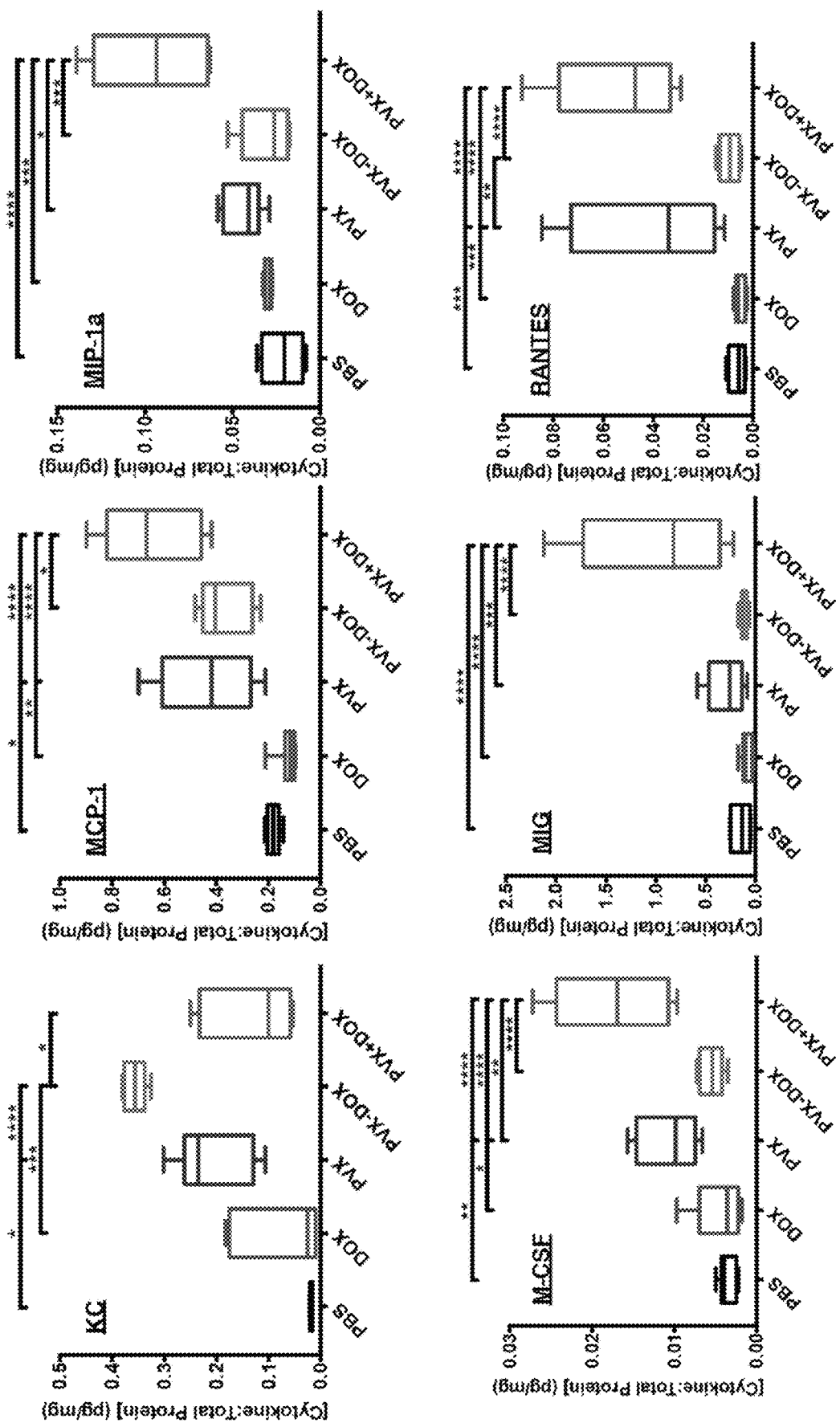

To gain insight into the underlying immunology we performed cytokine/chemokine profiling using a 32-plex MILLIPLEX® Luminex® assay. Tumors were treated with PBS, PVX, DOX, PVX-DOX, or PVX+DOX and harvested 24 hours after the first injection. Profiles were obtained using tumor homogenates and normalized to total protein levels by the bicinchoninic acid (BCA) assay. The PVX+DOX group repeatedly showed significantly higher particular cytokine and chemokine levels compared to any other group (FIG. 10). Specifically, interferon gamma (IFNγ) and IFNγ-stimulated or synergistic cytokines were elevated. These included, but may not be limited to: Regulated on Activation, Normal T Cell Expressed and Secreted (RANTES/CCL5), Macrophage Inflammatory Protein 1a (MIP-1a/CCL3), Monocyte Chemoattractant Protein (MCP-1/CCL2), Monokine Induced by Gamma interferon (MIG/CXCL9), and IFNγ-induced protein 10 (IP-10). IFNγ is a multifunctional type II interferon critical for inducing a pro-inflammatory environment and antiviral responses and is often associated with effective tumor immunotherapy responses. Under the influence of IFNγ, these chemokines mediate the influx of monocytes, macrophages, and other immune cells. Interestingly, the induction of IFNγ was not associated with the increased expression of its master positive regulator, IL-12, thus in this context, the increased expression of IFNγ is IL-12-independent (data not shown). In the tumor microenvironment, activation of the IFNγ pathway is in accordance with other work, where viruses were applied as an in situ vaccine. Stimulation of the IFNγ pathway alleviates the immuno-suppressive tumor microenvironment promoting an anti-tumor immune response. The molecular receptors and signaling cascades are yet to be elucidated, but the body of data indicates IFNγ to be a key player for viral-based in situ vaccination approaches.

Other noteworthy cytokines/chemokines that were up-regulated include interleukin-1β (IL-1β) and Macrophage Colony-Stimulating Factor (M-CSF). IL-1β is known to be an early pro-inflammatory cytokine activated by many PAMPs and Danger Associated Molecular Patterns (DAMPs). IL-1β signaling was also observed in our earlier work with CPMV, and data suggest that initial recognition of the viral in situ vaccine by innate surveillance cells is promoting immune activation. IL-1β and M-CSF are both major recruiters and activators of monocytes and macrophages to the site of challenge. M-CSF, in particular, enhances monocyte functions including phagocytic activity and cytotoxicity for tumor cells, while inducing synthesis of inflammatory cytokines such as IL-1, TNFα, and IFNγ in monocytes. PVX monotherapy appears to follow a similar trend of increased expression of cytokines/chemokines, with further enhanced response through combination with DOX when coadministered (PVX+DOX), but reduced response when directly coupled together as PVX-DOX.

In this example, we demonstrated that PVX stimulates an anti-tumor immune response when used as an in situ vaccine. Data indicate that the plant virus-based nanoparticles activate the innate immune system locally—this innate immune activation is thought to overcome the immunesuppressive tumor microenvironment re-starting the cancer immunity cycle leading to systemic elimination of cancer cells through the adaptive immune system. It is likely that innate receptors such as pattern recognition receptors (PRR) play a key role recognizing the multivalent nature of the plant virus nanoparticles; the repetitive, multidentate coat protein assemblies are products known as pathogen-associated molecular patterns (PAMPs).

The combination of the DOX chemotherapeutic with PVX was more efficacious than the monotherapies when co-administered as the PVX+DOX formulation, but not when physically linked in the PVX-DOX formulation. Data show that PVX+DOX induced a higher immune mediator profile within the tumor microenvironment, in turn resulting in increased efficacy against B16F10 melanoma. A key conclusion to draw from these studies is that the combination of chemo- and immunotherapy indeed is a powerful tool—yet the formulation of the two regimes into a single, multi-functional nanoparticle may not always be the optimal approach.

It has long been recognized that nanoparticles are preferentially ingested by phagocytic cells. FIG. 9C confirms this and shows that PVX-DOX is concentrated in F4/80+ macrophages within the tumor. The basis for reduced efficacy of PVX-DOX as compared to PVX+DOX could simply be because when phagocytes ingest PVX-DOX, it reduces the concentration of DOX available to react with tumor cell DNA. If as seems likely, the cells that respond to PVX at least initially are phagocytes, then a nonexclusive alternative could be that ingestion of PVX-DOX by phagocytes leads to a different response than ingest of PVX by itself by those cells, thus blunting the immune response stimulated by PVX.

Example 5

This example describes the use of PVX for delivery of doxorubicin (DOX), an FDA-approved anti-tumor drug used in treatments of various malignancies including breast cancer, ovarian cancer, acute lymphoblastic leukemia, Hodgkin's lymphoma, and small cell lung cancer. DOX is an anthracycline that kills cancer cells via three mechanisms of action: (1) intercalating with DNA, (2) inhibiting topoisomerase II, and (3) producing reactive oxygen species. However, like all chemotherapies, when administered systemically, it is associated with off-target effects due to non-specific interaction with healthy cells, ranging in severity from hair loss to heart failure. Herein, we loaded DOX onto the surface of PVX by hydrophobic interactions and characterized the therapeutic nanoparticles (DOX-loaded PVX) using transmission electron microscopy, gel electrophoresis, and UV/visible spectroscopy. The efficacy of the approach was then examined in a panel of cancer cells in vitro. Lastly, we assessed efficacy using a mouse model of triple negative breast cancer using MDA-MB-231 breast cancer xenografts in athymic mice.

Materials and Methods

Preparation of PVX

PVX was propagated in *Nicotiana benthamiana* plants and purified as previously reported.

Preparation and Characterization of DOX-Loaded PVX

Doxorubicin HCl (denoted as DOX) was purchased from INDOFINE Chemical Company. To prepare PVX-DOX, PVX (at 2 mg mL$^{-1}$ in 0.1 M potassium phosphate buffer (KP), pH 7.0) was incubated with a 5000 molar excess of DOX in a 10% (v/v) final concentration of DMSO for 5 days at room temperature, with agitation. PVX-DOX was purified twice over a 30% (w/v) sucrose cushion using ultracentrifugation (212,000×g for 3 h at 4° C.) and resuspended overnight in 0.1 M KP, pH 7.0. The particles were stored in 0.1 M KP, pH 7.0 at 4° C. until used.

To prepare therapeutic particles for the in vivo study, we also conjugated polyethylene glycol (PEG) using PEG-succinimidyl ester with a molecular weight of 5000 Da (PEG-NHS, purchased from Nanocs) to formulate PEG-PVX-DOX. PEG-NHS was added to the mixture of PVX and DOX on day 4 at 2000 molar excess of PVX and incubated overnight at room temperature. Following purification as described above, PVX, PVX-DOX, and PEG-PVX-DOX were characterized by transmission electron microscopy (TEM), agarose gel electrophoresis, denaturing gel electrophoresis (SDS-PAGE), and UV/visible spectroscopy.

Transmission electron microscopy (TEM) was performed after DOX loading to confirm integrity of PVX-DOX filaments. PVX-DOX samples (0.1 mg mL$^{-1}$, in dH$_2$O) were placed on carbon-coated copper grids and negatively stained with 0.2% (w/v) uranyl acetate. Grids were imaged using a Zeiss Libra 200FE transmission electron microscope, operated at 200 kV.

To confirm PVX-DOX association, PVX-DOX filaments were separated using a 0.8% (w/v) agarose gel (in 1×TBE buffer). PVX-DOX or PEG-PVX-DOX and corresponding amounts of free DOX or PVX alone were loaded with 6× agarose loading dye (Fisher Scientific).

Samples were run at 100 V for 30 min in TBE. Gels were visualized under UV light and white light before and after staining with 0.25% (w/v) Coomassie Blue (CB) staining, respectively.

SDS-PAGE was carried out to determine the number of PEG chains per PVX filament. 10 μg of denatured protein samples were analyzed on 4-12% NuPage gels (Life Technologies) in 1×MOPS SDS running buffer (Life Technologies). Protein bands were visualized under UV light and white light before and after staining with CB. Band density analysis was conducted using ImageJ 1.47d.

The number of DOX per PVX filament was determined by UV/visible spectroscopy using a NanoDrop 2000 spectrophotometer. PVX concentration and DOX loading were determined using the Beer-Lambert law and the DOX-(11, 500 $M^{-1}$ $cm^{-1}$ at 495 nm) and PVX-specific (2.97 mL $mg^{-1}$ $cm^{-1}$ at 260 nm) extinction coefficients.

Cell Culture

A2780, a gift from Dr. Analisa DiFeo (Case Western Reserve University) were cultured in Dulbecco's modified Eagle's media (DMEM, Life Technologies), supplemented with 10% (v/v) fetal bovine serum (FBS, Atlanta Biologicals) and 1% (v/v) penicillin-streptomycin (penstrep, Life Technologies). HeLa (ATCC) were cultured in minimum essential media (MEM, Life Technologies), supplemented with 10% (v/v) FBS, 1% (v/v) penstrep, and 1% (v/v) L-glutamine (Life Technologies). MDA-MB-231, a gift from Dr. Ruth Keri (Case Western Reserve University), were cultured in Roswell Park Memorial Institute (RPMI, Life Technologies) medium supplemented with 10% (v/v) FBS, 1% (v/v) penstrep, and 1% (v/v) L-glutamine. All cells were maintained at 37° C. and 5% $CO_2$.

Cytotoxicity Evaluation

Confluent cells were removed with 0.05% (w/v) trypsin-EDTA (Life Technologies), seeded at either $2\times10^3$ cells/100 µL/well (MDA-MB-231 and HeLa) or $5\times10^3$ cells/100 µL/well (A2780) in 96-well plates and grown overnight at 37° C., 5% $CO_2$. The next day, cells were washed 2 times with PBS and incubated with free DOX, PVX-DOX, or PEG-PVX-DOX corresponding to 0, 0.01, 0.05, 0.1, 0.5, 1, 5, or 10 µM (A2780, MDA-MB-231) or 0, 0.1, 0.5, 1, 5, 10, 25, or 50 NM (HeLa) DOX for 24 h, in triplicate. A PVX only control corresponded to the amount of PVX in the highest PVX-DOX sample. Following incubation, cells were washed 2 times to remove unbound DOX or particles. Fresh medium (100 µL) was added and cells were returned to the incubator for 48 h. Cell viability was assessed using an MTT proliferation assay (ATCC); the procedure was as the manufacturer suggested.

Tracking of Free DOX and PVX-DOX in Cells

A2780 cells were grown to confluency and removed with 0.05% (w/v) trypsin-EDTA. Cells were seeded at $1\times10$ 4 cells/500 µL/well on coverslips in untreated 24-well plates and grown overnight at 37° C., 5% $CO_2$. The next day, cells were washed 3 times and incubated with free DOX or PVX-DOX (1.5 µM DOX) for 2, 4, 12, 24, or 48 h. Following incubation, cells were washed 3 times and fixed in DPBS (Corning) containing 5% (v/v) paraformaldehyde (Electron Microscopy Sciences) and 0.3% (v/v) glutaraldehyde (Polysciences) for 10 min at room temperature. Coverslips were mounted using Fluoroshield (Sigma). Slides were imaged on a Zeiss Axio Observer Z1 motorized FL inverted microscope. Fluorescence intensity was analysed as follows using ImageJ 1.47d. All images were identically processed prior to fluorescence intensity measurement. Nuclei were selected and analyzed for fluorescence intensity using the measure feature of ImageJ. For each sample, a minimum of 3 images was analyzed and at least 4 cells were analyzed per image.

In Vivo Efficacy of PEG-PVX-DOX

All experiments were conducted in accordance with Case Western Reserve University's Institutional Animal Care and Use Committee. Female NCR nu/nu mice (6 weeks old) were injected subcutaneously into the right flank with $2\times10^6$ MDA-MB-231 cells suspended in 100 µL of media and Matrigel (Corning) at a 1:1 ratio. When tumors reached 100-200 $mm^3$, a dosage of 1.0 mg/kg body weight DOX was injected intravenously (this dosage corresponds to 1.0-2.0 mg PVX depending on batches). Groups of 4 animals each were treated with PEG-PVX-DOX, free DOX, or PBS. The dosage was normalized to the DOX content. Treatments were performed every 5 days, and a total of 5 treatments was given.

Tumors were measured daily and total volume was calculated using the formula:

$$v=(1\times w2)/2.$$ Mice were euthanized following 25 days of treatment.

Results

Synthesis and Characterization of DOX-Loaded PVX

PVX was produced through farming in *N. benthamiana* plants and purified using established protocols. From 100 g of infected leaf material, about 20 mg of pure PVX was extracted. DOX was loaded onto PVX by incubating excess DOX with the filaments in 0.1 M KP buffer (pH 7.0, final 10% (v/v) DMSO) for 5 days at room temperature (FIG. 11A). We used a 5000 molar excess of DOX per PVX; this was determined to be the optimized ratio that allowed homogenous mixing without aggregation. Further prolonged incubation time did not increase loading capacity (data not shown). The reaction was purified twice via ultracentrifugation. Purified DOX-loaded PVX (denoted as PVX-DOX) was characterized by TEM, agarose gel electrophoresis, and UV/visible spectroscopy (FIG. 11B-D).

First, TEM was used to confirm the particle integrity after loading DOX. The filamentous structure remained unchanged as seen from the TEM image (FIG. 11B). Agarose gel electrophoresis was used to confirm that DOX was associated to PVX and not free in solution. DOX is fluorescent when visualized under UV light and PVX was visualized under white light after Coomassie Blue (CB) staining. PVX is too large to migrate through the gel in 30 min, and remains confined to the well. Under UV light, no signal was seen in the PVX only lane, while PVX-DOX signal was seen directly within the well (FIG. 11C). The free DOX control, due to its positive charge, migrated towards the cathode. Imaging of the gels after staining with CB confirmed the presence of PVX and PVX-DOX in their respective wells; gel electrophoresis also indicates that DOX is stably associated with PVX. Finally, UV/visible spectroscopy was used to determine the number of DOX associated per PVX. The Beer-Lambert law, in conjunction with the PVX- and DOX-specific extinction coefficients, was used to determine the concentrations of both PVX and associated DOX in solution. The ratio of DOX to PVX concentration was then used to determine DOX loading. It was determined that PVX was loaded with 850-1000 DOX (FIG. 11D); the range indicates batch-to-batch variability. Noteworthy, the peak derived from DOX in PVX-DOX was red-shifted, indicating the association of DOX to PVX (FIG. 11D). PVX-DOX stability was confirmed after 1 month of storage at 4° C.; DOX release was not apparent (data not shown).

PVX-DOX Maintains Cell Killing Ability In Vitro

We next determined whether doxorubicin maintained its cell killing ability after being loaded onto PVX. Increasing amounts of PVX-DOX and corresponding free DOX were evaluated in a panel of cell lines: A2780 (ovarian cancer), MDA-MB-231 (breast cancer), and HeLa (cervical cancer) (FIG. 12A-D). The calculated $IC_{50}$ values of PVX-DOX were 0.84, 0.94, and 5.8 µM for A2780, MDA-MB-231, and HeLa, respectively (FIG. 12D).

Meanwhile, free DOX showed slightly lower values (indicating higher efficacy) at each corresponding cell line: 0.22, 0.13, and 1.6 µM (FIG. 12D). The calculated IC 5° values for free DOX are similar to previously reported values. PVX itself at the highest corresponding concentration exhibited no toxicity, thus attributing the cell killing function to the doxorubicin activity. A similar trend was observed in all tested cell lines: PVX-DOX was therapeutically active, but with decreased efficacy compared to free DOX (p<0.05).

Tracking of DOX and PVX-DOX in A2780 Cell Line

Figure 13A:
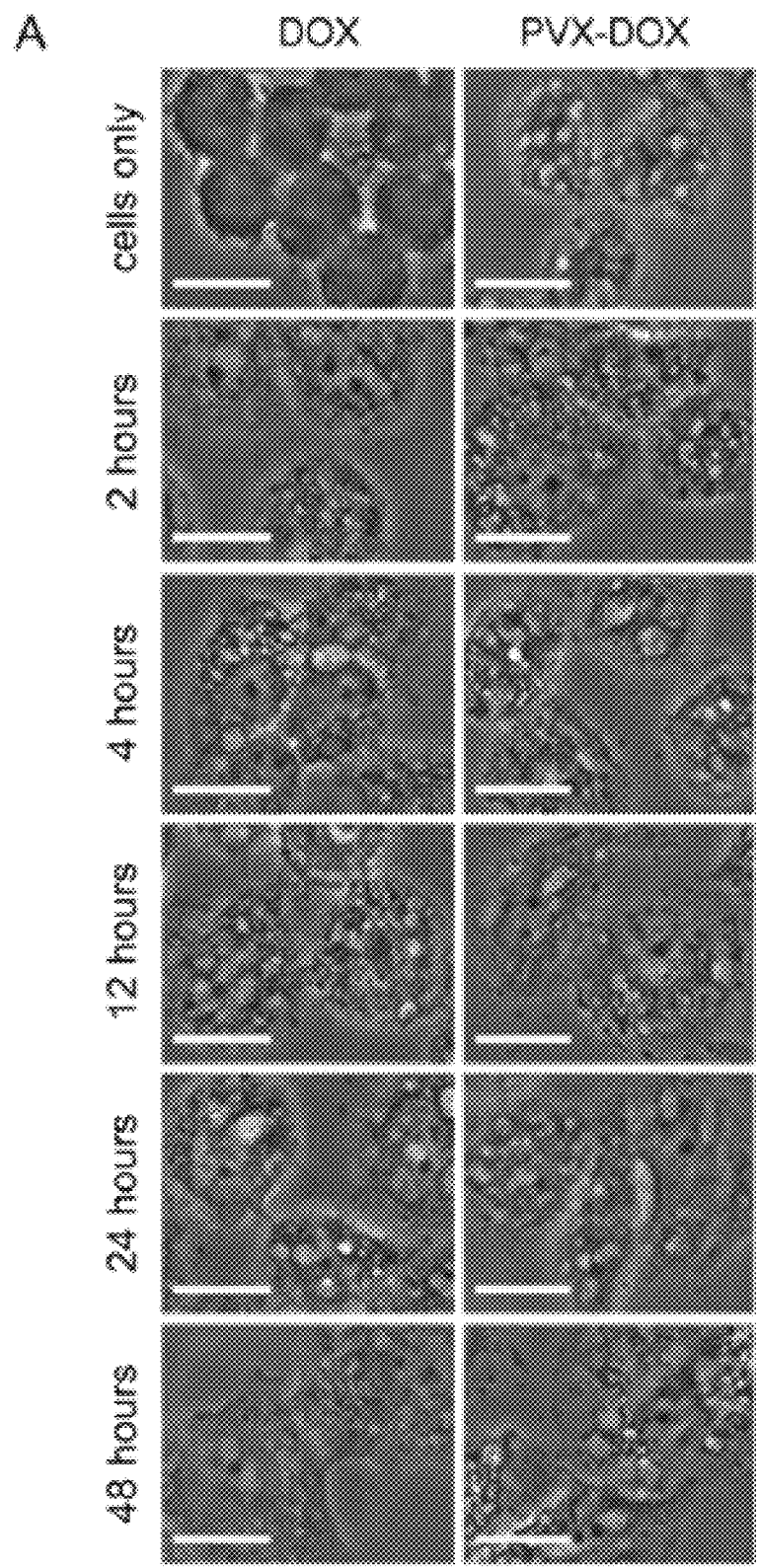
FIGS. 13(A-B) illustrate nuclear accumulation of DOX in A2780 cells after incubation with DOX or PVX-DOX over a 48 h time course. DOX accumulation was imaged (A) and quantified (B) using fluorescence microscopy. Scale bar=20 μm. For quantification, at least 3 images were analyzed per sample, with at least 4 cells per image considered. Fluorescence intensity (FI) was quantified by measuring the nuclei using ImageJ software.

The decreased efficacy of PVX-DOX vs. free DOX could be due to decreased uptake or inefficient release and trafficking of the PVX-DOX complex. To address these questions, we performed fluorescence microscopy studies to monitor DOX accumulation in the nucleus of treated cells. A2780 cells were incubated with 1.5 µM of DOX (either as PVX-DOX or free DOX) for 2, 4, 12, 24, or 48 h and imaged using a fluorescence microscope. DOX fluorescence per cell was analysed using ImageJ software (FIG. 13). As reported in previous studies, DOX accumulated within the nucleus, where it was visible via fluorescence. DOX within the cytoplasm is not fluorescent due to scattering and absorption by cellular components. Additionally, DOX is more concentrated within the nucleus than when it is dispersed throughout the cytoplasm; increased concentration of DOX is correlated to increases in fluorescence intensity. Up until 24 h, the accumulation of DOX in the nucleus increased over time, as shown by increased fluorescence observed in cells treated with either PVX-DOX or free DOX (FIG. 13A). At 48 h, treated cells were undergoing apoptosis leading to reduced DOX fluorescence—drug-induced apoptosis was apparent for cells treated with either PVX-DOX or free DOX attesting to the efficacy of the PVX-based delivery system.

Quantitative analysis of the images indicated that PVX-DOX exhibited lower nuclear accumulation compared to free DOX at all time points tested (FIG. 13B). However, the decrease was only statistically significant (p<0.05) at 24 and 48 h.

Preparation of PEGylated PEG-PVX-DOX Nanoparticles

To assess the efficacy of PVX-DOX in vivo, we prepared a PEGylated formulation. Like other nanoparticles, PVX is cleared by the mononuclear phagocyte system (MPS) when administered systemically. Conjugation of stealth polymers such as PEG, however, decreases serum protein adsorption, resulting in the "stealth properties" that enhance circulation time and decrease accumulation in liver and spleen. We previously reported that PEGylated PVX coated with linear PEG chains with a molecular weight of 5000 Da demonstrates enhanced in vivo fates and favourable tumor accumulation.

To prepare PEG-PVX-DOX, PEG-NHS (using a 2000 molar excess of PEG to PVX) was added into the mixture of PVX and DOX on day 4 (FIG. 14A). Excess DOX and PEG were removed by two rounds of ultracentrifugation. We used agarose gel and denaturing gel (SDS-PAGE) electrophoresis to confirm the loading of DOX and attachment of PEG. Agarose gel electrophoresis indicated that free DOX was completely removed from the solution and the fluorescence was only derived from DOX associated with PVX (FIG. 14B). Additionally, SDS-PAGE (FIG. 14C) confirmed successful conjugation of PEG to the PVX coat protein. Under UV light, DOX, released from its PVX carrier, is detectable at the bottom of gel. Nevertheless, dim fluorescence was observed from the PVX coat proteins (~25 kDa) indicating that some amounts of DOX remained associated with the protein even after exposure to denaturing conditions and electrophoretic separation. Analysis by ImageJ indicates that 95-97% of DOX was released from the denatured PVX. After staining by CB, the PVX coat protein and an additional band at a higher molecular weight corresponding to the PEGylated coat protein was observed in PEG-PVX-DOX but not PVX-DOX. To estimate the degree of PEGylation (number of PEG chains per PVX particle), band density analysis was performed using ImageJ About 10% of PVX coat proteins were modified with PEG. Finally, the UV/visible spectrum indicated that about 1000-1500 DOX were loaded per particle (FIG. 14D); the range indicates the batch-to-batch variability. A red shift of the DOX-derived absorbance peak was also observed for PEG-PVX-DOX (as in PVX-DOX), indicating the association of DOX with the PEGylated PVX (FIG. 14D). Data show that higher loading of DOX to the PEGylated vs. native PVX is achieved. The increase in DOX loading might be because attached PEG chains further entrapped free DOX.

In Vitro and In Vivo Efficacies of PEG-PVX-DOX

Figure 15C:
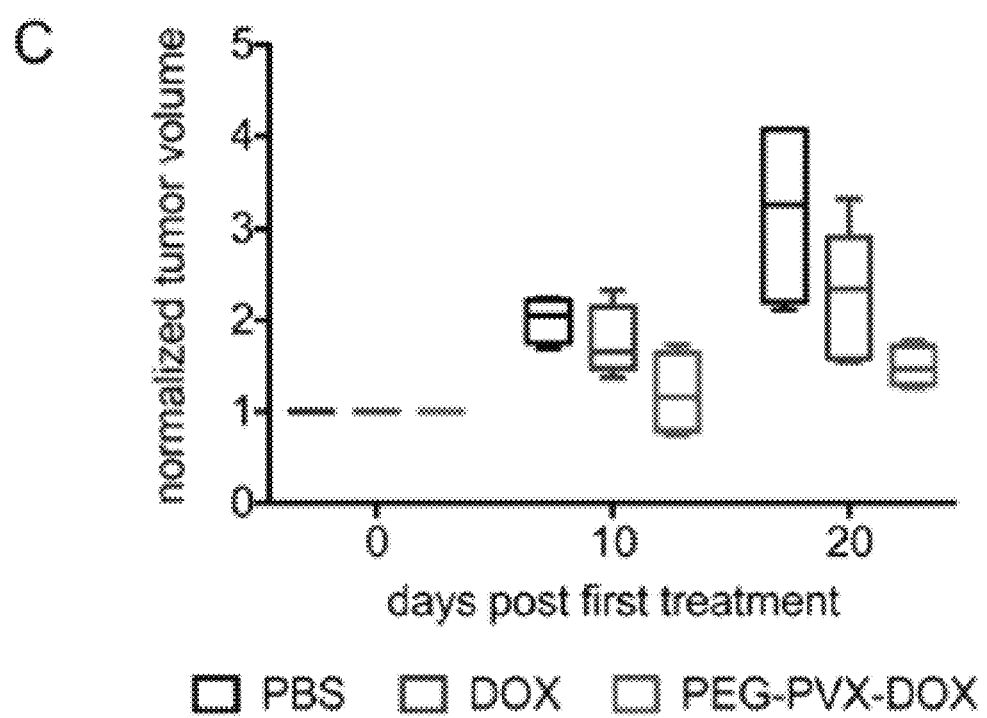
FIGS. 15(A-C) illustrate (A) In vitro efficacy of PEG-PVX-DOX vs. DOX determined by MTT assay. DOX or PEG-PVX-DOX corresponding to 0, 0.01, 0.05, 0.1, 0.5, 1, 5, or 10 μM were incubated with MDA-MB-231 cells. $IC_{50}$ values were determined using GraphPad Prism software (DOX vs. PVX-DOX p<0.05). (B,C) Treatment of MDA-MB-231 tumors in an athymic mouse model using PEG-PVX-DOX vs. DOX and PBS. Treatment started when tumors reached 100-200 mm³; arrows indicate the treatment schedule. Groups of 4 animals were treated with a dosage of 1.0 mg/kg body weight DOX or PEG-PVX-DOX normalized to the DOX dose. (B) Daily monitored tumor volume growth in mice of different groups and (C) tumor volumes normalized to initial tumor volumes at day 0, 10, and 20 post first treatment (middle bars represent median values and the whiskers denote the minimum and maximum values).

We chose a model of triple negative breast cancer to assess the efficacy of PEG-PVX-DOX. First, in vitro efficacy was tested using MDA-MB-231 cells to confirm cell killing of the PVX-based drug carrier after PEGylation. Increasing amounts of PEG-PVX-DOX and free DOX were added to the culture media for 24 h then cells were washed and efficacy determined using an MTT assay. Analogous to PVX-DOX, PEG-PVX-DOX had cell killing ability but decreased efficacy compared to free DOX (FIG. 15A). The efficacy of PEG-PVX-DOX was 0.78 µM, which is about 6-fold higher than that of free DOX (0.13 µM). There is no significant difference in efficacies with and without PEG (FIGS. 12D and 15A).

Next, we investigated the capacity of PEG-PVX-DOX to inhibit tumor growth using MDA-MB-231 tumor-bearing athymic mouse model. Treatments were started when the tumor volume reached 100-200 mm$^3$. The dosage of DOX on the carrier as well as free DOX was 1 mg/kg body weight. Intravenous injections into the tail vein were performed every 5 days for a total of 5 injections. Tumor volumes were measured daily. Statistically significant differences in mice treated with PBS or free DOX were only observed after day 22 post first treatment (FIG. 15B). In contrast, statistical significant differences between PBS vs PEG-PVX-DOX were apparent from day 7 post first treatment (p<0.05) (FIG. 15B). At the end of the treatment, tumor volumes in PEG-PVX-DOX treated group were 2.6 times smaller, while ones in DOX treated group were 2.1 times smaller than the PBS control. While data did not show statistical significance between DOX vs. PEG-PVX-DOX at the end of the treatment, a trend was apparent indicating that tumor volumes were smaller when mice were treated with PEG-PVX-DOX compared to the controls; this trend was observed throughout the study and indicates effective inhibition of tumor growth mediated by the plant virus—based drug delivery formulation (FIG. 15B, C).

We tested the efficacy of PVX-DOX in vitro in a panel of DOX-sensitive cell lines: A2780 (ovarian cancer), MDA-MB-231 (breast cancer), and HeLa (cervical cancer) using the MTT assay. There was a similar trend in these models: PVX-DOX exhibited cell killing, but with decreased efficacy compared to free DOX. However, these results are not unexpected; similar trends have been reported with synthetic and virus-based nanoparticles for DOX delivery. The reason for the lower efficacy may be explained by the lower uptake of DOX in the nucleus when delivered as PVX-DOX vs. free DOX (as was shown through longitudinal cell imaging using A2780 cells, see FIG. 13A). Differences in DOX uptake could be explained by uptake mechanisms of free DOX versus PVX-delivered DOX. Free DOX is taken up via diffusion across the cell membrane, while VNPs such as PVX are likely taken up by endocytosis or macropinocytosis. Thus, it is possible that PVX-delivered DOX is not as readily taken up as free DOX, resulting in decreased accumulation over time. Indeed, nuclear fluorescence intensity from PVX-DOX is approximately ⅔ of the nuclear fluorescence intensity measured for free DOX after 24 h of incubation. In comparison, DOX killed A2780 cells 4 times more effectively than PVX-DOX. The non-linear relationship between the imaging results and the MTT assay may be explained by the differences in experimental set up: nuclear fluorescence intensity was determined 24 h post-exposure to DOX or PVX-DOX; however, for cell viability, cells were incubated with DOX or PVX-DOX for 24 h followed by an additional 48 h incubation time. Thus, the differences between DOX and PVX-DOX may be more profound in the MTT assay vs. the imaging study.

Nevertheless, the in vitro assays do not reflect the complexity of the in vivo situation. In vivo additional biological barriers must be considered—and biodistribution and clearance for free and PVX-formulated DOX will not follow the same trend. The conclusion to be drawn from the in vitro studies are that even though the $IC_{50}$ indicates reduced efficacy of the nanoparticle formulation vs. free DOX, the PVX-DOX formulations maintains cell killing efficacy.

Finally, we prepared the stealth therapeutic nanoparticle PEG-PVX-DOX for evaluation of the in vivo efficacy in the MDA-MB-231-bearing athymic mouse model. PEGylation did not alter the cell killing ability (FIG. 15A). In a mouse model of triple negative breast cancer, we observed that PEG-PVX-DOX outperformed free DOX (FIG. 15B, C), highlighting the potential of PVX as a drug carrier.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating cancer in a subject in need thereof, comprising administering directly to the cancer a therapeutically effective amount of an in situ vaccine, the in situ vaccine including at least one of potato virus X (PVX) or PVX virus-like particles, and an anti-cancer agent, wherein the PVX or PVX virus-like particles are not used as a vehicle for drug or antigen delivery.

2. The method of claim 1, wherein the in situ vaccine is administered intratumorally.

3. The method of claim 1, wherein the anti-cancer agent is provided in a formulation with the in situ vaccine that is administered directly to the cancer.

4. The method of claim 1, wherein the anti-cancer agent is doxorubicin.

5. The method of claim 1, wherein the cancer is metastatic cancer.

6. The method of claim 1, wherein the cancer is selected from the group consisting of melanoma, breast cancer, colon cancer, lung cancer, and ovarian cancer.

7. The method of claim 1, wherein the cancer is lung cancer and wherein the in situ vaccine is administered by inhalation.

8. A method of treating cancer in a subject in need thereof, comprising administering to the subject therapeutically effective amounts of an anti-cancer agent and an in situ vaccine, wherein the in situ vaccine includes at least one of potato virus X (PVX) or virus-like particles, the PVX or PVX virus like particles and the anti-cancer agent are administered directly to the cancer, and wherein the PVX or PVX virus-like particles are not used as a vehicle for drug or antigen delivery.

9. The method of claim 8, wherein the in situ vaccine is administered intratumorally.

10. The method of claim 8, wherein the anti-cancer agent is doxorubicin.

11. The method of claim 8, wherein the cancer is metastatic cancer.

12. The method of claim 8, wherein the cancer is selected from the group consisting of melanoma, breast cancer, colon cancer, lung cancer, and ovarian cancer.

13. The method of claim 8, wherein the cancer is lung cancer and wherein the in situ vaccine is administered by inhalation.

14. The method of claim 1, wherein the cancer is dermal melanoma and the in situ vaccine is administered intratumorally.

15. The method of claim 1, further comprising the step of ablating the cancer by treating the subject with a therapeutically effective amount of radiotherapy, chemotherapy, high intensity focused ultrasound or immunotherapy.

16. The method of claim 15, wherein the treating by chemotherapy comprises the administration of an additional anticancer agent to the subject in a therapeutically effective amount.

17. The method of claim 15, wherein the treating by immunotherapy comprises the administration of monoclonal antibodies to the subject in a therapeutically effective amount.

18. The method of claim 8, wherein the anti-cancer agent is monoclonal antibodies.

19. The method of claim 8, wherein the cancer is dermal melanoma and the in situ vaccine is administered intratumorally.

20. The method of claim 1, wherein the subject is a mammalian subject.

* * * * *